US011173237B2

(12) United States Patent
Mallipalli et al.

(10) Patent No.: US 11,173,237 B2
(45) Date of Patent: *Nov. 16, 2021

(54) AMMONIA DETECTION IN DIALYSIS SYSTEMS

(71) Applicant: Fresenius Medical Care Holdings, Inc., Waltham, MA (US)

(72) Inventors: Harshavardhana Reddy Mallipalli, Edmond, OK (US); Philip Scott James, Orinda, CA (US); Ethan Lee Zimbra, Walnut Creek, CA (US); Kerissa Adams, Norman, OK (US); Troy Dayton, Syracuse, UT (US); Jon F. Moss, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/945,474

(22) Filed: Jul. 31, 2020

(65) Prior Publication Data
US 2020/0405937 A1      Dec. 31, 2020

Related U.S. Application Data

(63) Continuation of application No. 16/455,276, filed on Jun. 27, 2019, now Pat. No. 10,765,793.

(51) Int. Cl.
  *G01N 31/22*   (2006.01)
  *A61M 1/16*    (2006.01)
  *B01D 61/32*   (2006.01)

(52) U.S. Cl.
  CPC ........ *A61M 1/1696* (2013.01); *A61M 1/1605* (2014.02); *B01D 61/32* (2013.01);
  (Continued)

(58) Field of Classification Search
  CPC ............ G01N 21/256; G01N 21/3151; G01N 21/6428; G01N 21/274; B01L 3/502;
  (Continued)

(56) References Cited

U.S. PATENT DOCUMENTS 4,248,973 A   2/1981  Kallies
4,548,906 A   10/1985 Sekikawa et al.
(Continued)

FOREIGN PATENT DOCUMENTS

CN    108535248    9/2018
DE    102010055883  6/2012
(Continued)

OTHER PUBLICATIONS

Fresenius Medical Care Power Point, "Ammonium Sensor Chemistry DOE," dated Oct. 25, 2018, 9 pages.
(Continued)

*Primary Examiner* — Hoa Q Pham
(74) *Attorney, Agent, or Firm* — Fish & Richardson P.C.

(57) ABSTRACT

A spectroscopic detection system includes a sensor configured to reflect light of a first wavelength associated with a presence of a reference substance on the sensor and configured to reflect light of a second wavelength associated with a presence of a monitored substance on the sensor, wherein the monitored substance flows to the sensor from a circulating fluid. The spectroscopic detection system further includes a detector that has first and second channels for respectively receiving the light of the first and second wavelengths reflected from the sensor and one or more processors in electrical communication with the detector and configured to identify an excess condition of the monitored substance with respect to the circulating fluid based on a ratio of a second amount of the light of the second wave-
(Continued)

length received at the detector to a first amount of the light of the first wavelength received at the detector.

22 Claims, 33 Drawing Sheets

(52) U.S. Cl.
CPC . *A61M 2205/18* (2013.01); *A61M 2205/3306* (2013.01); *A61M 2205/50* (2013.01); *A61M 2205/587* (2013.01)

(58) Field of Classification Search
CPC ...... A61M 1/696; A61M 1/605; A61M 1/165; A61M 1/1613; A61M 1/1619; B01J 20/048; B01J 20/08; B01J 20/06; B01J 20/28052; B01J 20/0292
USPC ................ 356/432–440, 300–326; 210/188; 436/52, 108, 113, 133, 163
See application file for complete search history.

(56) References Cited

U.S. PATENT DOCUMENTS

| | | | |
|---|---|---|---|
| 5,198,335 | A | 3/1993 | Sekikawa et al. |
| 5,629,533 | A | 5/1997 | Ackley et al. |
| 6,887,051 | B2 | 5/2005 | Sakuda et al. |
| 8,409,864 | B2 | 4/2013 | Ash |
| 8,945,936 | B2 | 2/2015 | Ash |
| 9,138,524 | B2 | 9/2015 | Bluchel et al. |
| 9,599,599 | B2 | 3/2017 | Ash |
| 9,707,328 | B2 | 7/2017 | Pudil et al. |
| 9,827,361 | B2 | 11/2017 | Pudil et al. |
| 10,765,793 | B1 | 9/2020 | Mallipalli et al. |
| 2002/0068364 | A1 | 6/2002 | Arai et al. |
| 2003/0003589 | A1 | 1/2003 | Khalil et al. |
| 2003/0113931 | A1 | 6/2003 | Pan |
| 2005/0180879 | A1 | 8/2005 | Hrboticka |
| 2006/0263253 | A1 | 11/2006 | Steuerwald et al. |
| 2006/0263257 | A1 | 11/2006 | Beuchamp et al. |
| 2007/0134740 | A1 | 6/2007 | Brusilovsky et al. |
| 2007/0161113 | A1 | 7/2007 | Ash |
| 2008/0076184 | A1 | 3/2008 | Putnam et al. |
| 2014/0190876 | A1 | 7/2014 | Meyer et al. |
| 2015/0226702 | A1 | 8/2015 | Veltman et al. |
| 2015/0367057 | A1 | 12/2015 | Gerber et al. |
| 2018/0073989 | A1 | 3/2018 | Lura et al. |
| 2021/0069399 | A1* | 3/2021 | Egley .................. A61M 1/1664 |

FOREIGN PATENT DOCUMENTS

| | | |
|---|---|---|
| WO | WO 04/090511 | 10/2004 |
| WO | WO 2009/064984 | 5/2009 |
| WO | WO 2011/017215 | 2/2011 |
| WO | WO 2012/161744 | 11/2012 |

OTHER PUBLICATIONS

PCT International Search Report and Written Opinion in International Appln. No. PCT/US2020/037260, dated Sep. 17, 2020, 11 pages.
Puskas, "Ammonium Sensor Design and Testing," Fresenius Medical Care, dated Feb. 7, 2019, 9 pages.

* cited by examiner

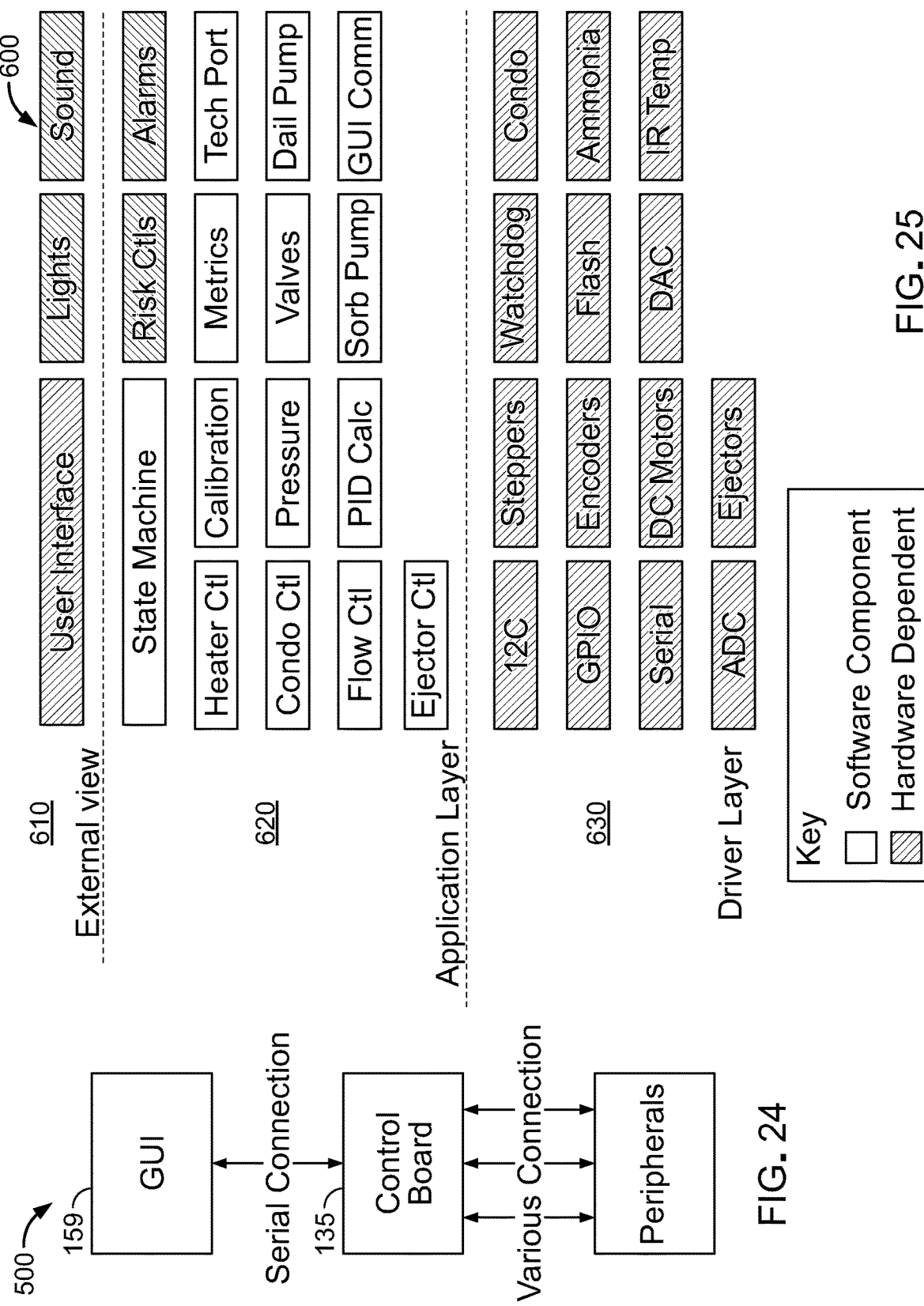

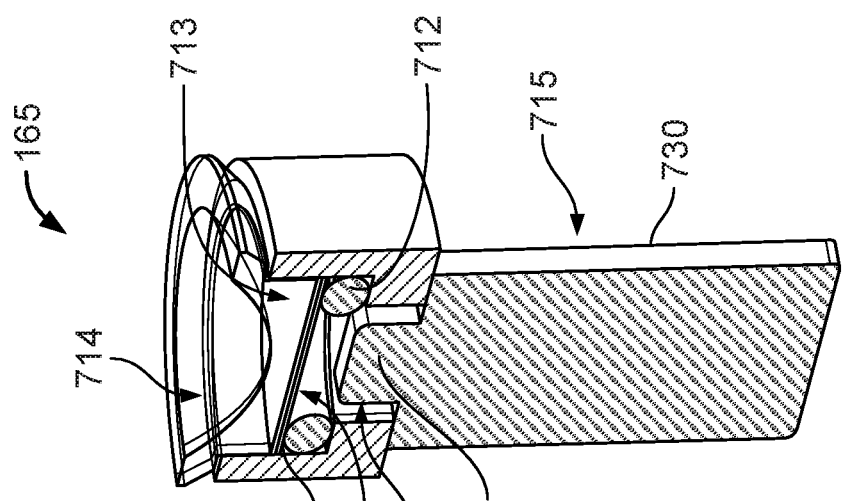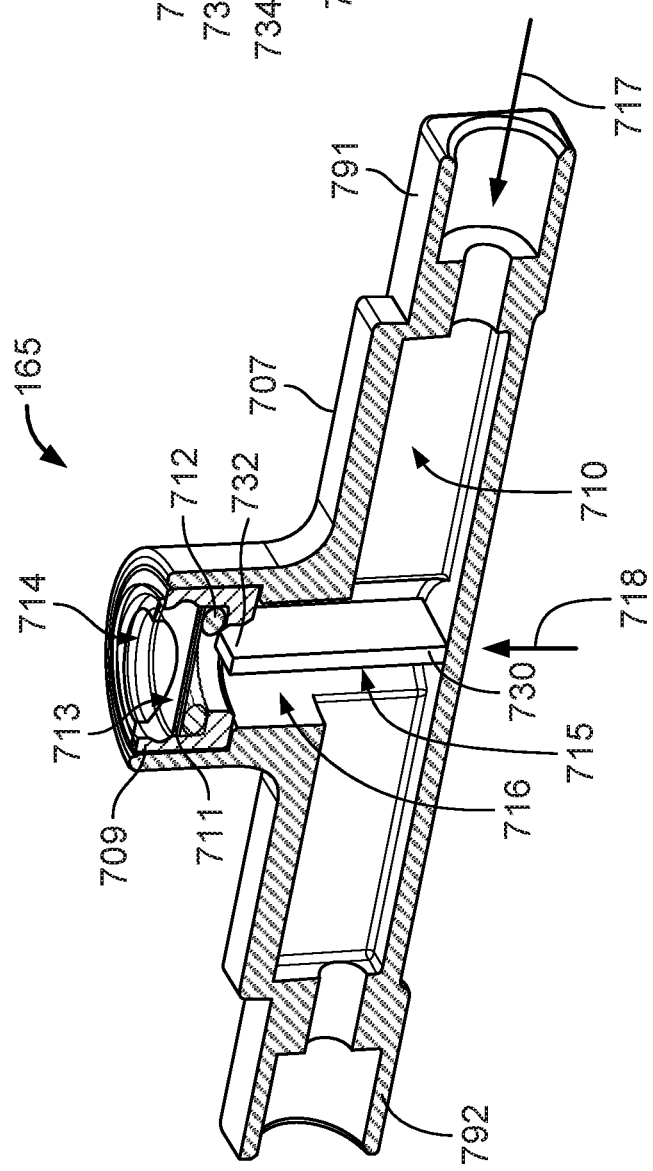

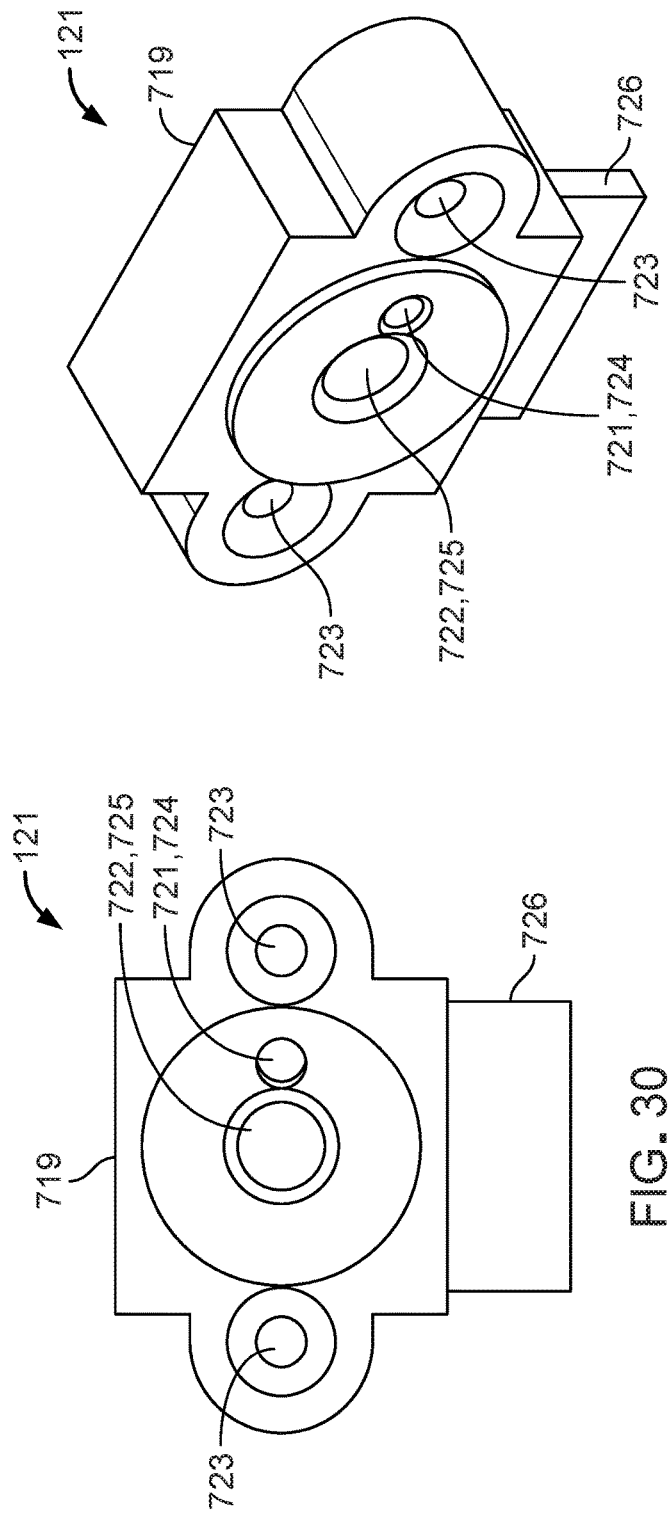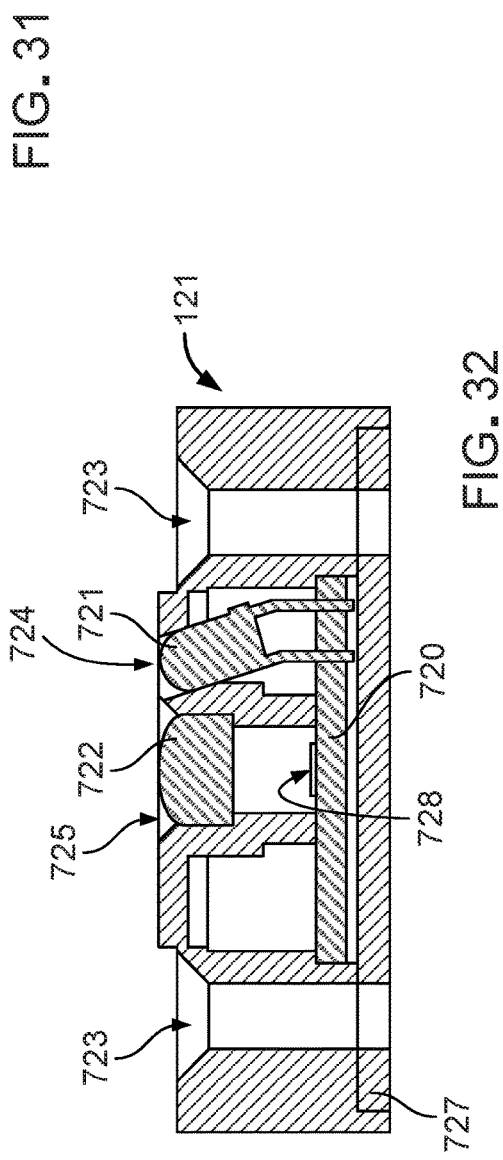
FIG. 30
FIG. 31
FIG. 32

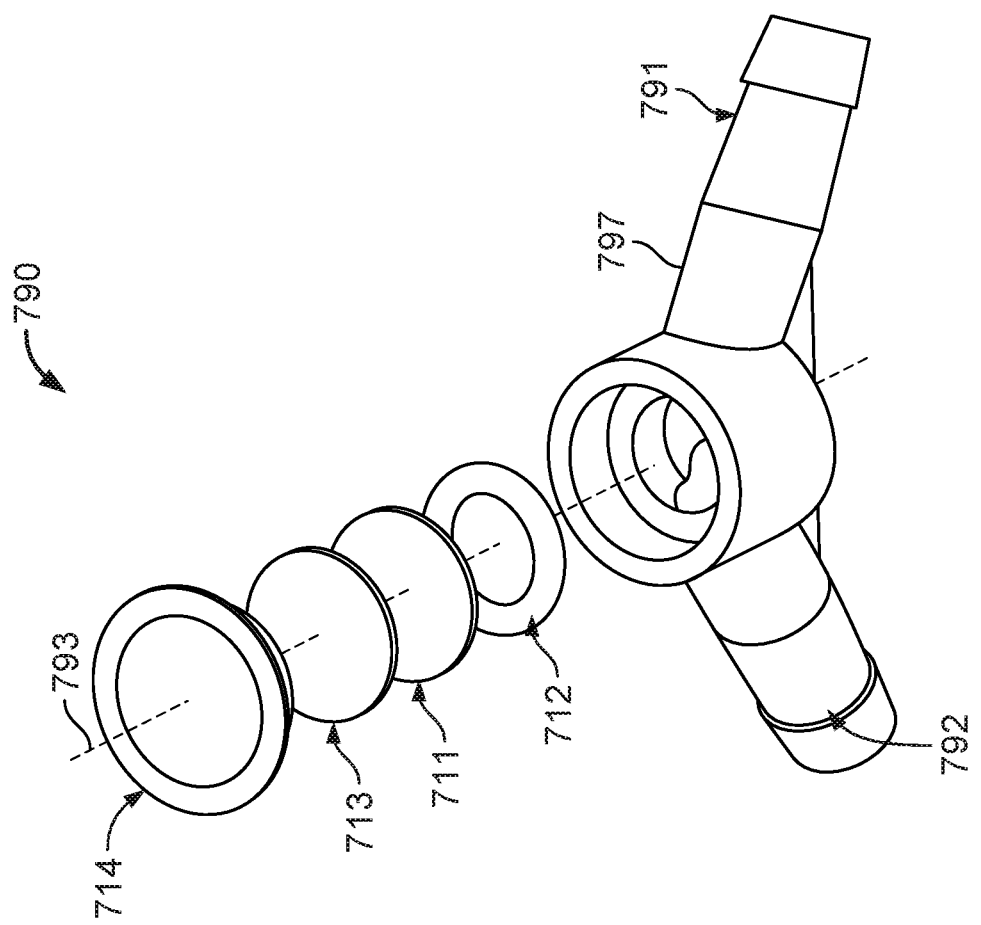

AMMONIA DETECTION IN DIALYSIS SYSTEMS

CROSS-REFERENCE TO RELATED APPLICATIONS

This application is a continuation application of and claims priority to U.S. application Ser. No. 16/455,276, filed on Jun. 27, 2019.

TECHNICAL FIELD

This disclosure relates to fluid conditioning systems for generating and conditioning dialysis fluid utilized by dialysis machines to carry out dialysis treatments. Such fluid conditioning systems can include mechanisms for detecting ammonia within the dialysis fluid.

BACKGROUND

Dialysis is a medical treatment that provides life-saving support to patients with insufficient renal function. The two principal dialysis methods are hemodialysis (HD) and peritoneal dialysis (PD). During HD, the patient's blood is passed through a dialyzer of a dialysis machine, while a dialysis solution (or, dialysate) is also passed through the dialyzer, generally in an opposite or countercurrent direction. A semi-permeable membrane within the dialyzer separates the blood from the dialysate and allows fluid exchanges to take place between the dialysate and the blood stream via diffusion, osmosis, and convective flow. These exchanges across the membrane result in the removal of waste products (e.g., such as solutes, like urea and creatinine) from the blood. These exchanges also help regulate the levels of other substances (e.g., sodium and water) in the blood. In this way, the dialyzer and dialysis machine act as an artificial kidney for cleansing the blood.

During PD, the patient's peritoneal cavity is periodically infused with dialysate. The membranous lining of the patient's peritoneum acts as a natural semi-permeable membrane that allows diffusion and osmosis exchanges to take place between the solution within the peritoneal cavity and the blood stream. Like HD, these exchanges across the patient's peritoneum result in the removal of waste products from the blood and help regulate the levels of other substances (e.g., sodium and water) in the blood.

Some dialysis systems also include a sorbent cartridge for regenerating (e.g., recycling) dialysate, substantially reducing the amount of dialysate needed to effect a complete treatment session. The sorbent cartridge can be designed to remove ammonium from the dialysate. However, the capacity of such cartridges to adsorb ammonium can diminish over time such that undesirable amounts of ammonium and ammonia may accumulate in the dialysate.

SUMMARY

This disclosure relates to fluid conditioning systems for generating and conditioning dialysis fluid utilized by dialysis machines to carry out dialysis treatments. In some embodiments, a fluid conditioning system includes an ammonia detection system embodied as a spectroscopic detection system for monitoring an amount of ammonia in dialysis fluid that circulates within the fluid conditioning system. The amount of ammonia within the dialysis fluid reflects an extent of ammonium leakage into the dialysis fluid as the dialysis fluid circulates through a sorbent cartridge of the fluid conditioning system.

In one aspect, a spectroscopic detection system includes a sensor configured to reflect light of a first wavelength associated with a presence of a reference substance on the sensor and configured to reflect light of a second wavelength associated with a presence of a monitored substance on the sensor, wherein the monitored substance flows to the sensor from a circulating fluid. The spectroscopic detection system further includes a detector that has first and second channels for respectively receiving the light of the first and second wavelengths reflected from the sensor and one or more processors in electrical communication with the detector and configured to identify an excess condition of the monitored substance with respect to the circulating fluid based on a ratio of a second amount of the light of the second wavelength received at the detector to a first amount of the light of the first wavelength received at the detector.

Embodiments may include one or more of the following features.

In some embodiments, the sensor includes an acid base indicator that is sensitive to a pH of the monitored substance.

In certain embodiments, the reference substance is an acidic substance, wherein the sensor is of a first color in an initial state in which the reference substance is present on the sensor and in which the monitored substance is not present on the sensor, and wherein the sensor is of a second color in a subsequent state in which both the reference substance and the monitored substance are present on the sensor.

In some embodiments, the spectroscopic detection system further includes one or more lenses arranged to focus the light of the first and second wavelengths reflected from the sensor onto the detector.

In certain embodiments, the spectroscopic detection system further includes an LED that is configured to radiate broadband light onto the sensor, wherein the sensor is configured to reflect a first portion of the broadband light as the light of the first wavelength and a second portion of the broadband light as the light of the second wavelength.

In some embodiments, the spectroscopic detection system further includes a membrane that is permeable to the monitored substance and positioned upstream of the sensor.

In certain embodiments, the spectroscopic detection system further includes a housing that supports the sensor and that is configured to absorb ambient light.

In some embodiments, the sensor is oriented parallel to a bulk flow direction of the circulating fluid and orientated perpendicular to a flow of the monitored substance towards the sensor.

In certain embodiments, the spectroscopic detection system further includes a flow obstruction that is oriented perpendicular to the bulk flow direction of the circulating fluid and that generates turbulence in a bulk flow of the circulating fluid.

In some embodiments, the flow obstruction is configured to increase a velocity of the bulk flow of the circulating fluid.

In certain embodiments, the sensor includes a paper material.

In some embodiments, the spectroscopic detection system further includes a connector body that houses the sensor and that is configured to be assembled with a fluid line of a fluid cassette, wherein the connector body is arranged to receive a bulk flow of the circulating fluid from a device configured to remove a precursor chemical of the monitored substance from the circulating fluid.

In certain embodiments, the first amount of the light of the first wavelength includes a first percent reflectance of a first color associated with the light of the first wavelength, and the second amount of the light of the second wavelength includes a second percent reflectance of a second color associated with the light of the second wavelength.

In some embodiments, the excess condition includes an increase in a concentration of the monitored substance within the circulating fluid, and the increase in the concentration of the monitored substance corresponds to an increase in a concentration of a precursor chemical of the monitored substance to value that is about equal to or greater than a threshold concentration of the precursor chemical.

In certain embodiments, the one or more processors are configured to identify the excess condition by determining a moving average of the ratio.

In some embodiments, the one or more processors are configured to identify the excess condition by determining a rate of change of the ratio.

In certain embodiments, the one or more processors are configured to identify the excess condition by comparing the moving average of the ratio to one or more criteria.

In some embodiments, the one or more processors are configured to transmit data associated with triggering of an alarm notification upon identification of the excess condition.

In certain embodiments, the sensor is disposable and the detector is reusable.

In some embodiments, the circulating fluid is dialysate and the monitored substance is ammonia.

In another aspect, a dialysis system includes a sorbent cartridge configured to remove a precursor substance from dialysate circulating through the dialysis system, where the precursor substance is a precursor to a monitored substance, and the dialysis system further includes a spectroscopic detection system for identifying an excess condition of the monitored substance with respect to the dialysate. The spectroscopic detection system includes a sensor configured to reflect light of a first wavelength associated with a presence of a reference substance on the sensor and configured to reflect light of a second wavelength associated with a presence of a monitored substance on the sensor, wherein the monitored substance flows to the sensor from the dialysate. The spectroscopic detection system further includes a detector that has first and second channels for respectively receiving the light of the first and second wavelengths reflected from the sensor and one or more processors in electrical communication with the detector and configured to identify an excess condition of the monitored substance with respect to the circulating fluid based on a ratio of a second amount of the light of the second wavelength received at the detector to a first amount of the light of the first wavelength received at the detector.

In another aspect, a method of detecting a monitored substance within a circulating fluid includes flowing the monitored substance to a sensor from the circulating fluid, reflecting light of a first wavelength from the sensor based on a presence of a reference substance on the sensor and reflecting light of a second wavelength from the sensor based on a presence of the monitored substance on the sensor, receiving the light of the first and second wavelengths reflected from the sensor respectively within first and second channels of a detector, and identifying, at one or more processors in electrical communication with the detector, an excess condition of the monitored substance with respect to the circulating fluid based on a ratio of a second amount of the light of the second wavelength received at the detector to a first amount of the light of the first wavelength received at the detector.

Embodiments may provide one or more of the following advantages.

In some embodiments, analyzing reflectance at the sensor as a ratio of blue color and red color intensities serves to amplify the detection of ammonia in the circulating dialysate, as compared to analyzing reflectance at a sensor as absolute values of separate, individual blue and red color intensities according to conventional reflectance spectroscopy techniques for ammonia detection. For example, both the numerator and the denominator of the reflectance ratio can change, whereas conventional techniques simply account for an absolute value of either a blue color intensity or an absolute value of a red color intensity of light reflected from an ammonium sensor. Therefore, examining the reflectance as a ratio can avoid false alarm conditions that may otherwise be observed due to temperature-associated changes in reflectance spectroscopy using conventional techniques during a phase in which dialysate is heated to physiological temperature. In some examples, a moving average technique is applied to reflectance ratio data to advantageously smoothen a curve of percent reflectance ratio, thereby minimizing effects due to noise factors.

In some examples, undesired effects of natural variations on an absolute value of the percent reflectance ratio may be addressed by examining a rate of change of the percent reflectance ratio. For example, such undesired effects (e.g., temperature-related effects) and various noise factors may have a shorter duration in a slope analysis of the percent reflectance ratio as compared to a duration in the absolute value of the percent reflectance ratio. Additionally, events such as lens fogging may also persist for a shorter time period in the slope analysis.

Other aspects, features, and advantages will be apparent from the description, the drawings, and the claims herein.

DESCRIPTION OF DRAWINGS

FIG. 24 provides a block diagram of a hardware system of the fluid conditioning system of FIG. 1.

FIG. 25 provides a block diagram of a software system of the fluid conditioning system of FIG. 1.

FIG. 27 is a cross-sectional perspective view of an ammonia sensor of the ammonia detection system of FIG. 26.

FIG. 28 is a cross-sectional perspective view of a baffle of the ammonia sensor of FIG. 27.

FIG. 30 is a top view of an ammonia detector of the ammonia detection system of FIG. 26.

FIG. 31 is a perspective view of the ammonia detector of FIG. 30.

FIG. 32 is a cross-sectional view of the ammonia detector of FIG. 30.

FIG. 39 is an exploded perspective view of an ammonia sensor that can be utilized with a cooperating ammonia detector.

DETAILED DESCRIPTION

Figure 1:
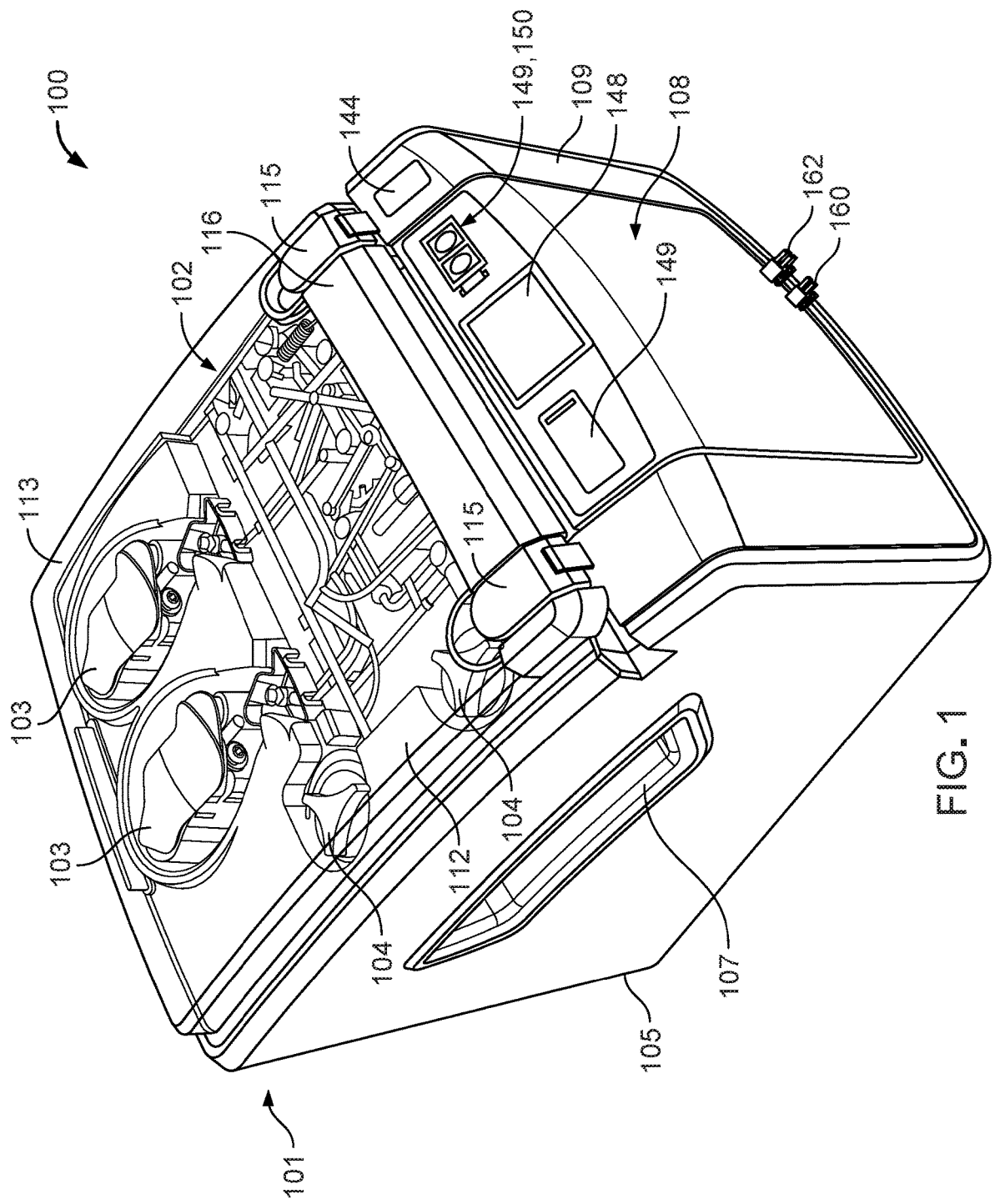
FIG. 1 is a perspective view of a fluid conditioning system that can cooperate with a dialysis system to carry out a fluid conditioning cycle that includes a dialysis treatment.
Figure 2:
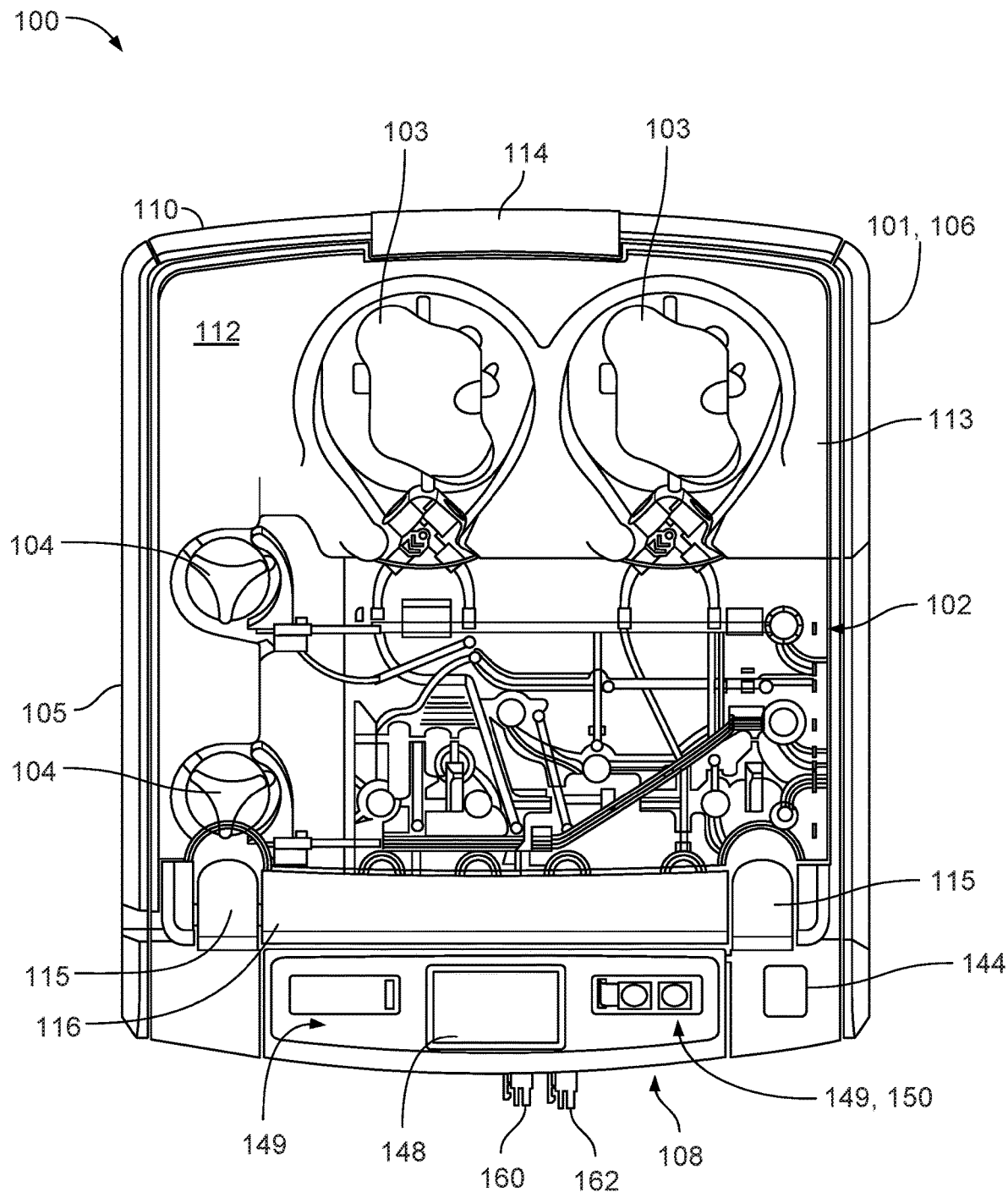
FIG. 2 is a top view of the fluid conditioning system of FIG. 1.
Figure 3:
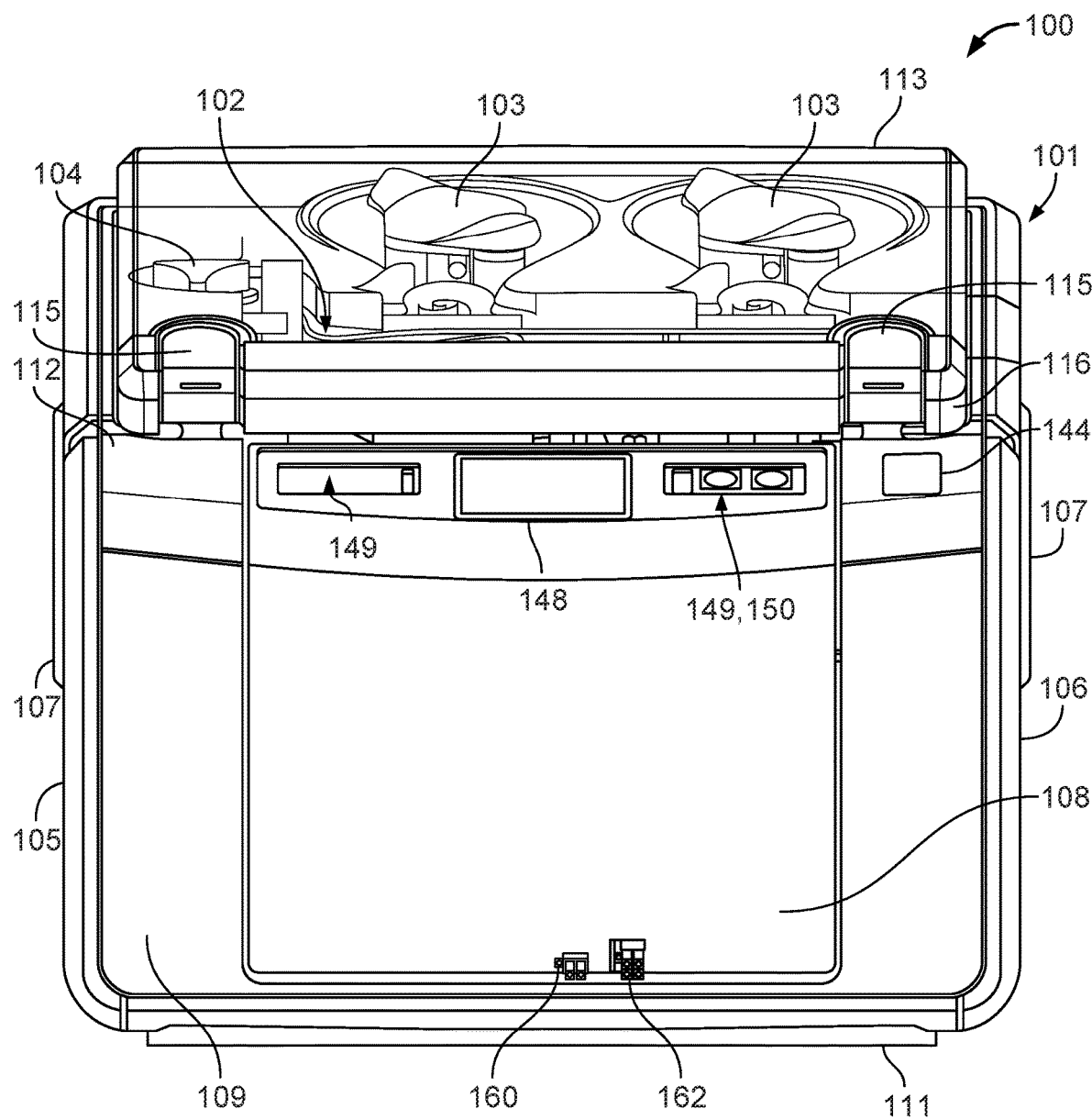
FIG. 3 is a front view of the fluid conditioning system of FIG. 1.
Figure 4:
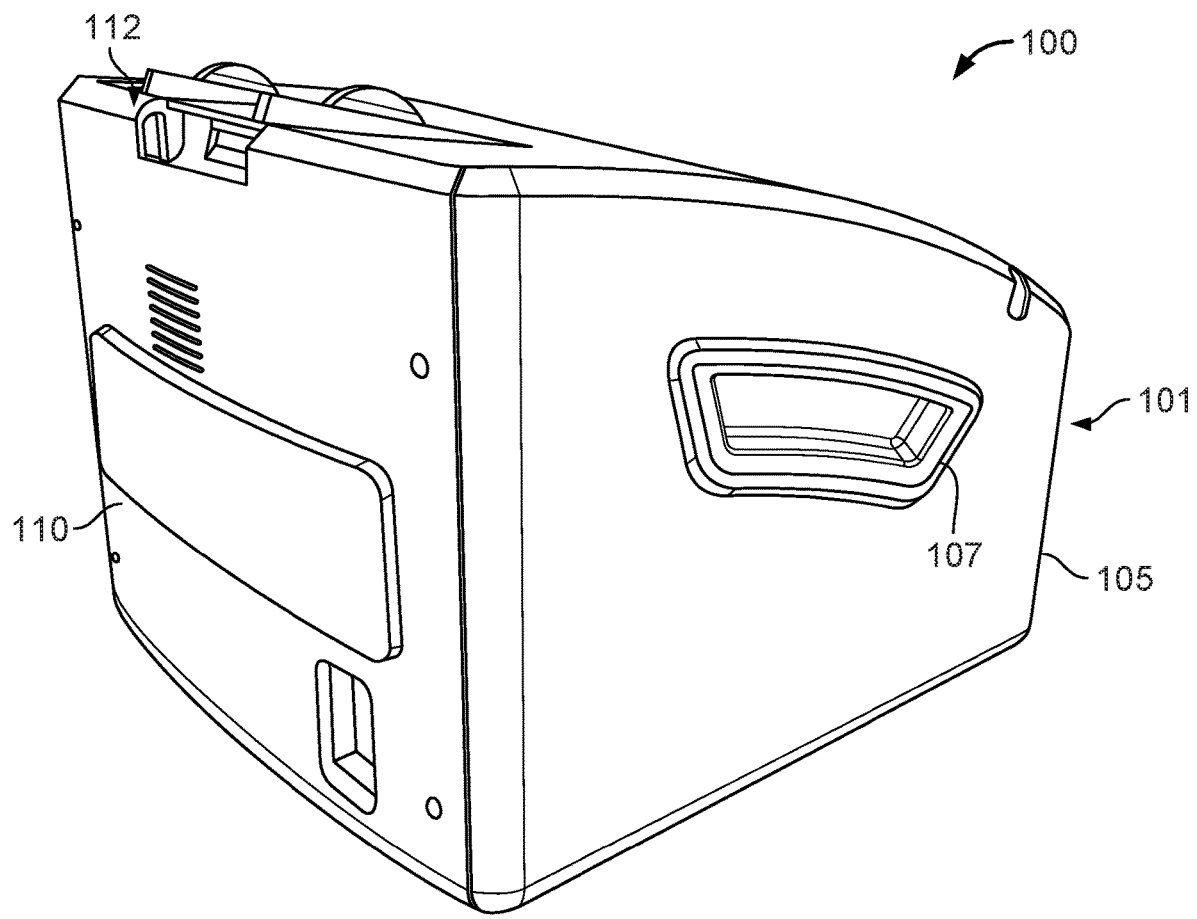
FIG. 4 is a rear view of the fluid conditioning system of FIG. 1.

FIGS. 1-4 illustrate a fluid conditioning system 100 that can be operated to prepare conditioned dialysate for use in a dialysis system. For example, the fluid conditioning system 100 can be fluidly communicated with the dialysis system to deliver "fresh" (e.g., cleaned, conditioned) dialysate to the dialysis system, collect "spent" (e.g., contaminated, unconditioned) dialysate from the dialysis system, and regenerate (e.g., cleanse) and condition the spent dialysate in a continuous fluid flow loop to recycle the spent dialysate. Example dialysis systems with which the fluid conditioning system 100 can be fluidly communicated include hemodialysis (HD) systems, peritoneal dialysis (PD) systems, hemofiltration (HF), hemodiafiltration (HDF) and other related systems.

The fluid conditioning system 100 includes a housing 101 that contains or supports components of the fluid conditioning system 100, a fluid cassette 102 that includes multiple fluid lines defining various fluid pathways, two relatively high capacity pumps 103 that can circulate fluid within the fluid lines of the fluid cassette 102, and two relatively low capacity pumps 104 that can deliver (e.g., infuse) conditioning agents into the fluid circulating within the fluid lines of the fluid cassette 102. The fluid conditioning system 100 has a compact footprint that facilitates lifting and transport of the fluid conditioning system 100. For example, the fluid conditioning system 100 typically has a length of about 30 cm to about 50 cm, a width of about 30 cm to about 50 cm, a height of about 30 cm to about 50 cm, and a weight of about 15 kg to about 20 kg.

The housing 101 includes left and right side panels 105, 106, handles 107 positioned along the side panels 105, 106 for carrying the fluid conditioning system 100, a door assembly 108 that can be opened and closed to insert a heater bag, a front panel 109 to which the door assembly 108 is secured, rear and bottom panels 110, 111 that further enclose the interior components, an upper panel 112 that supports the fluid cassette 102 and the pumps 103, 104, and a cover 113 that protects the fluid cassette 102 and the pumps 103, 104. Example materials from which the exterior panels of the housing 101 may be made include plastics, such as acrylonitrile butadiene styrene (ABS) and polycarbonate blends, among others.

The cover 113 is typically made of ABS or polycarbonate and is transparent or translucent to allow visualization of the fluid cassette 102 and the pumps 103, 104. The cover 113 can be pivoted at a rear hinge 114 disposed along the upper panel 112 to open or close the cover 113. The upper panel 112 carries two latches 115 that can be closed upon a front edge 116 of the cover 113 to secure the cover 113 in a closed position. The latches 115 can also be pulled up and apart from the cover 113 to release the cover 113 from the closed position for accessing the fluid cassette 102 and the pumps 103, 104.

Figure 5:
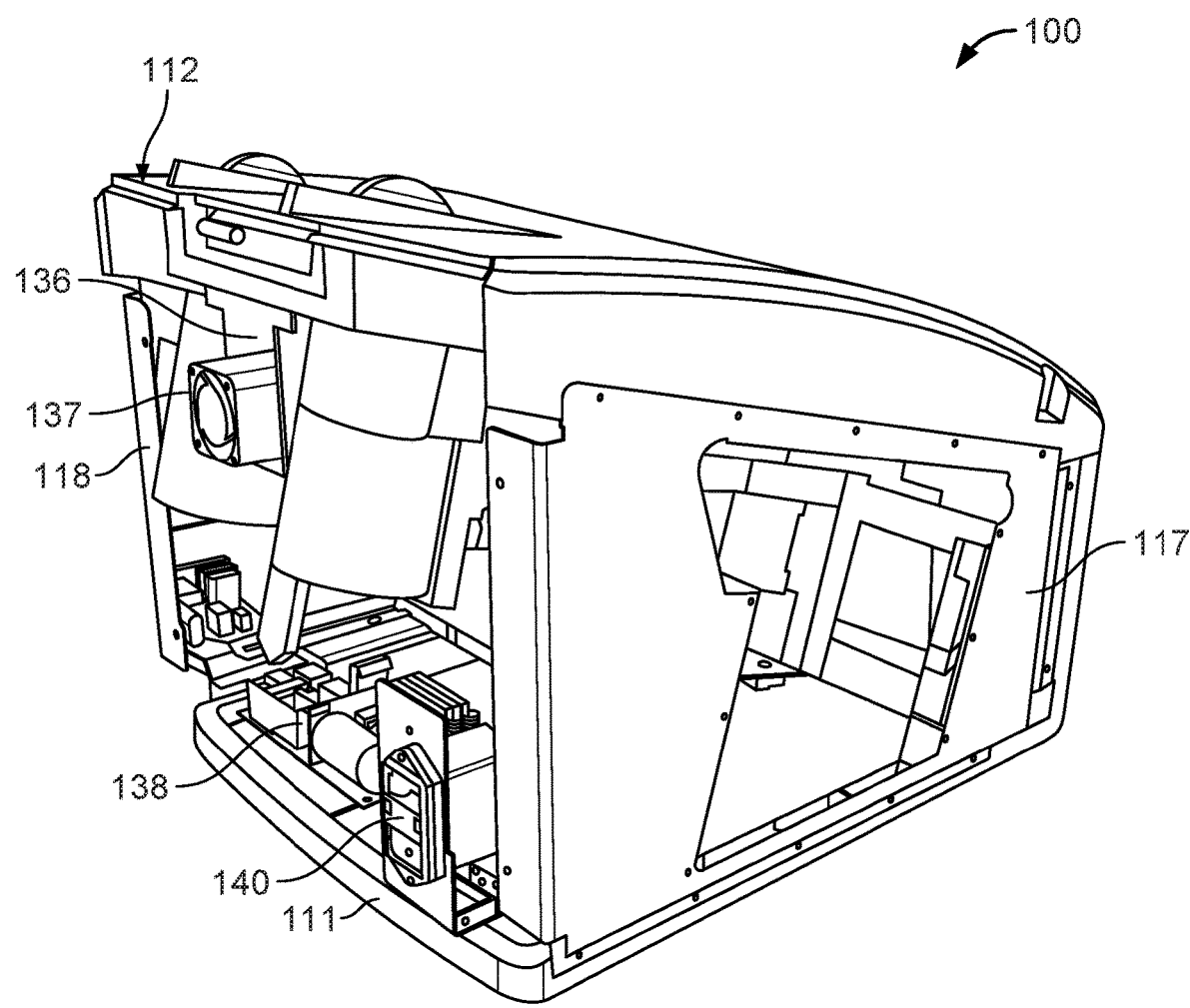
FIG. 5 is a rear view of the fluid conditioning system of FIG. 1, with certain exterior components omitted to expose certain interior components.

Referring to FIG. 5, the fluid conditioning system 100 also includes left and right side interior support frames 117, 118 to which the left side, right side, front, rear, bottom, and upper panels 105, 106, 109, 110, 111, 112 are attached. The interior support frames 117, 118 are typically formed from sheet metal.

Each pump 103, 104 is a peristaltic pump that includes multiple rollers positioned about the circumference of a rotatable frame (e.g., a motor) that carries a fluid line extending from the fluid cassette 102. As the rotatable frame is rotated, the rolling members apply pressure to the fluid line, thereby forcing fluid to flow through the fluid line.

Figure 6:
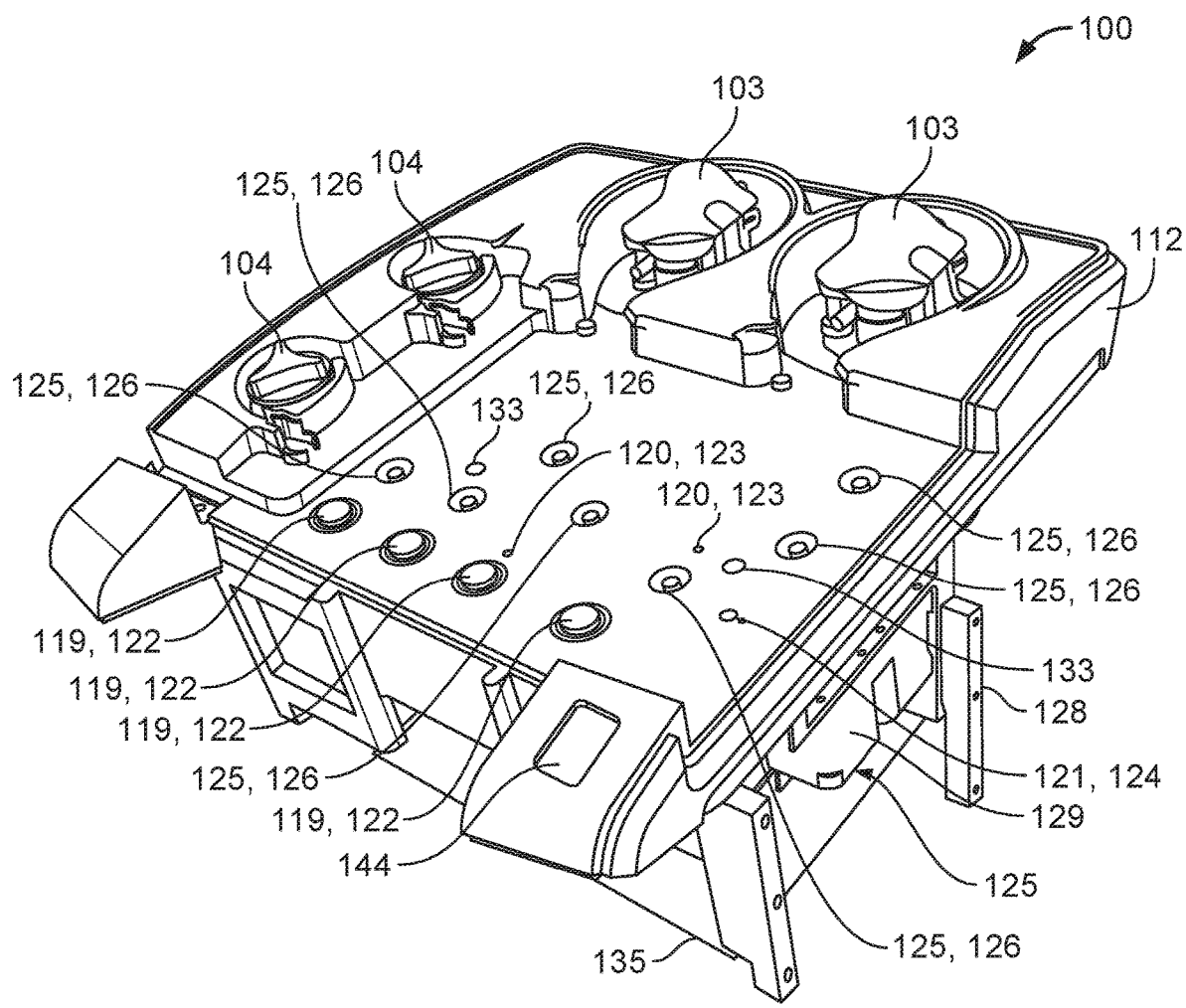
FIG. 6 is a perspective view of the fluid conditioning system of FIG. 1, with certain exterior components omitted to expose certain interior components.
Figure 7:
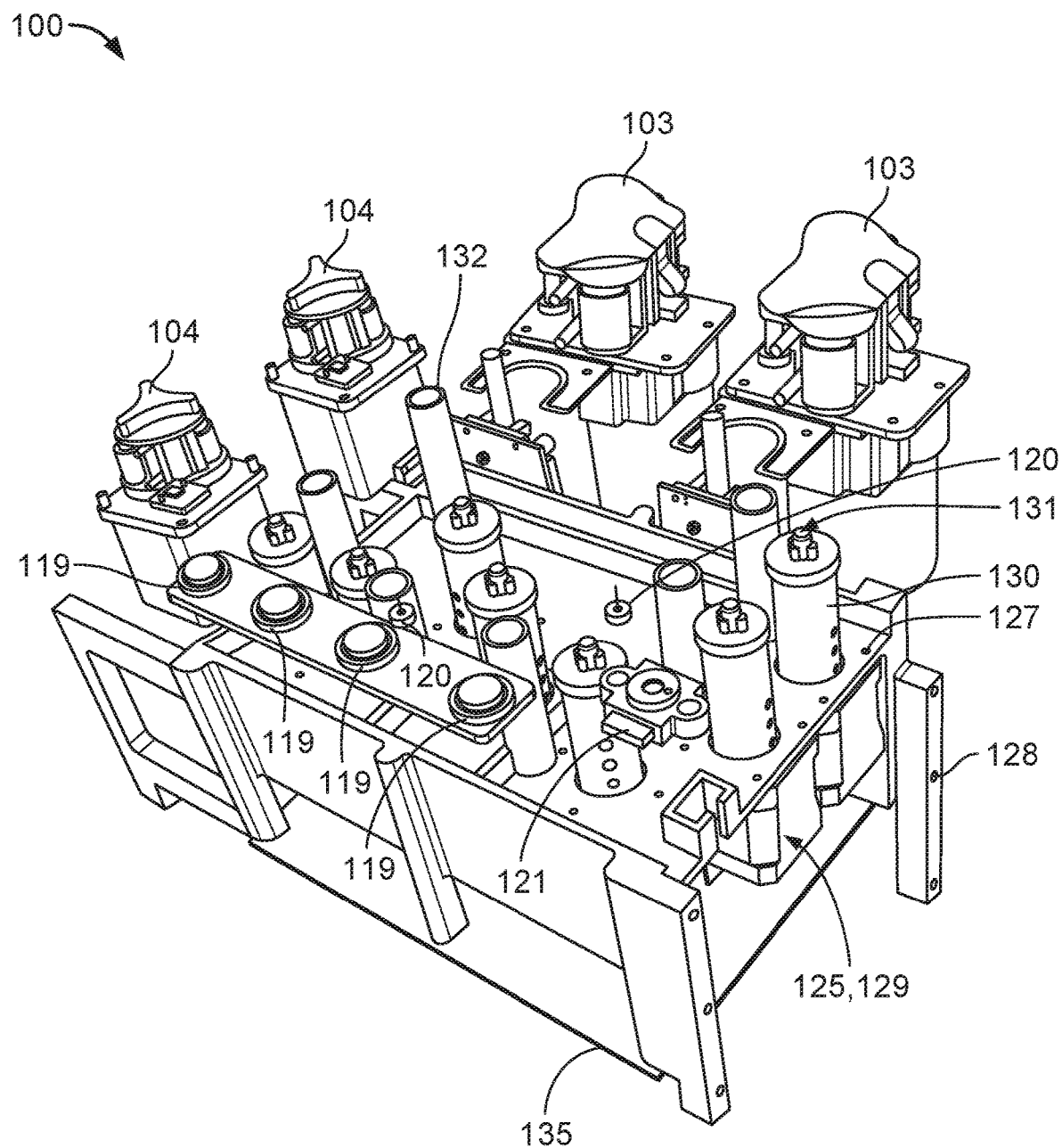
FIG. 7 is a perspective view of the fluid conditioning system of FIG. 1, with certain exterior components omitted to expose certain interior components.
Figure 8:
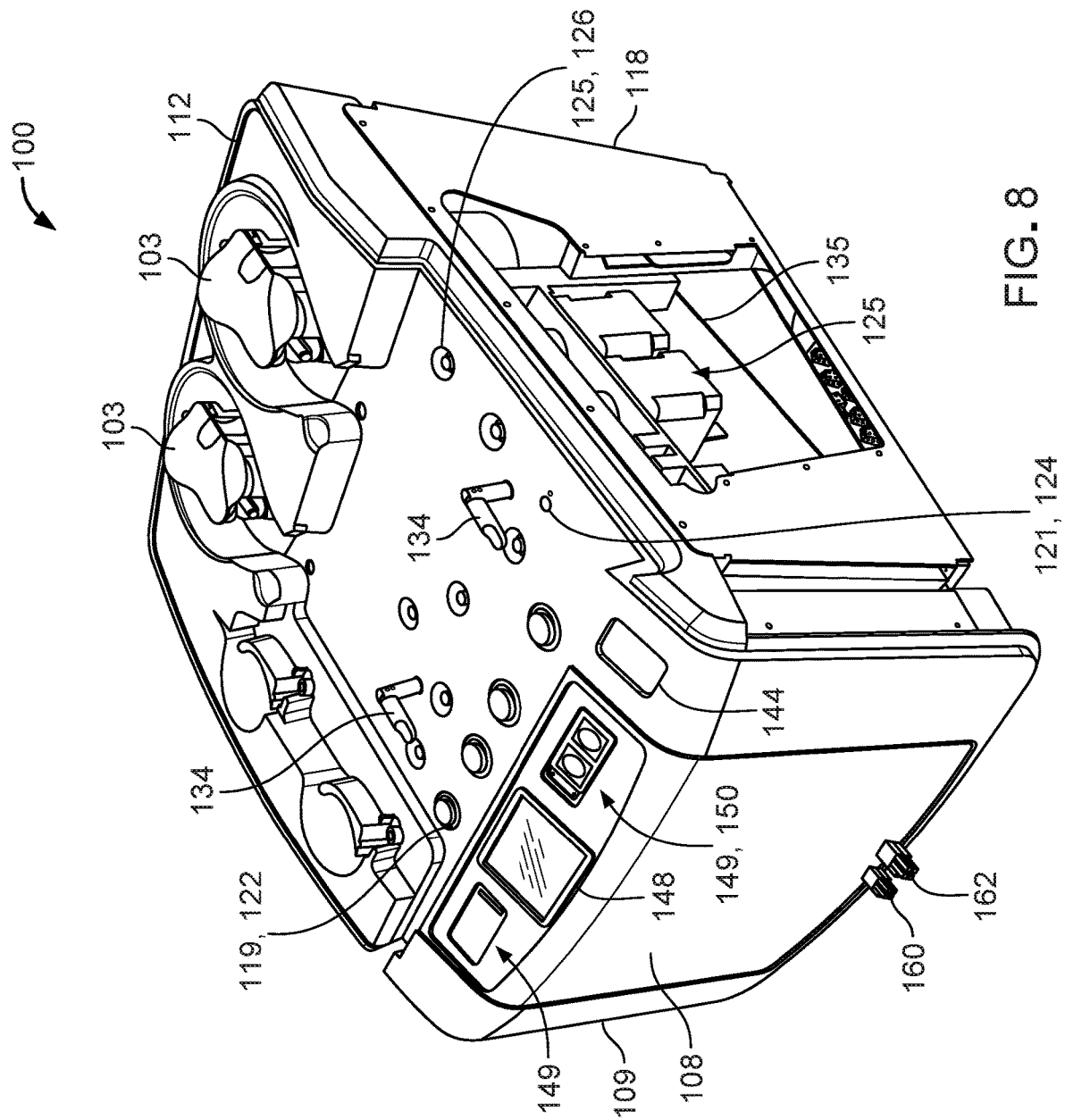
FIG. 8 is a perspective view of the fluid conditioning system of FIG. 1, with certain exterior components omitted to expose certain interior components.

FIGS. 6-8 illustrate certain interior components of the fluid conditioning system 100. For example, the fluid conditioning system 100 further includes multiple pressure transducers 119, two temperature sensors 120, and an ammonia detector 121 that are respectively positioned within holes 122, 123, 124 in the upper panel 112 for engagement with the fluid cassette 102. The pressure transducers 119 are embodied as thin, flexible membranes that contact corresponding thin, flexible membranes 164 within the fluid cassette 102 (refer to FIG. 15) for detecting fluid pressures within certain fluid pathways of the fluid cassette 102. The temperature sensors 120 are infrared (IR) sensors that detect temperatures of the dialysate flowing through certain points of the fluid pathways of the fluid cassette 102. The ammonia detector 121 is a red-green-blue (RGB) color sensor that can detect color changes on a paper strip within the fluid cassette 102 for determining a concentration of ammonium (e.g., which generates ammonia) within the dialysate flowing through a certain fluid pathway of the fluid cassette 102. The fluid conditioning system 100 also includes circuitry that acquires and conditions signals generated by conductivity sensors that are provided on the fluid cassette 102, which will be discussed in more detail below.

The fluid conditioning system 100 also includes multiple actuators 125 that are aligned with holes 126 in the upper panel 112 for respectively and selectively moving multiple valves of the fluid cassette 102. Each actuator 125 is mounted to a platform 127 of an internal frame 128 of the fluid conditioning system 100 and includes a motor 129 and a drive unit 130 that can be moved (e.g., rotated or otherwise manipulated) by the motor 129. The drive unit 130 is equipped with a coupling member 131 that is formed to engage a respective valve of the fluid cassette 102 such that movement of the drive unit 130 produces movement of the valve. The internal frame 128 also includes columnar support members 132 that support and locate the upper panel 112 of the housing 101. The upper panel 112 further defines holes 133 that are positioned and sized to receive locating pins 134 for appropriately positioning the fluid cassette 102 with respect to the upper panel 112. With the fluid cassette 102 in place, the locating pins 134 can be snapped down toward the upper panel 112 to lock the position of the fluid cassette 102. The fluid conditioning system 100 also includes a circuit board 135 equipped with electronics for operating the various electromechanical components of the fluid conditioning system 100. For example, the electronics execute codes for carrying out the various stages of a fluid conditioning cycle (as discussed below with reference to FIGS. 18-20), operating the pumps 103, 104, turning valves for the fluid cassette 102, processing sensor signals, operating the actuators 125, operating a heater assembly 151, and running control loops (e.g., control loops for regulating dialysate temperature, regulating pump speeds to achieve desired flow rates, regulating pump speeds to achieve desired dialysate chemical compositions, and ensuring device safety).

Referring again to FIG. 5, the fluid conditioning system 100 further includes a support bracket 136 and a fan 137 carried therein for cooling the circuit board 135 and other internal components of the fluid conditioning system 100. The fluid conditioning system 100 also includes a power supply 138, as well as a support bracket 139 that carries an A/C-in port 140.

Figure 10:
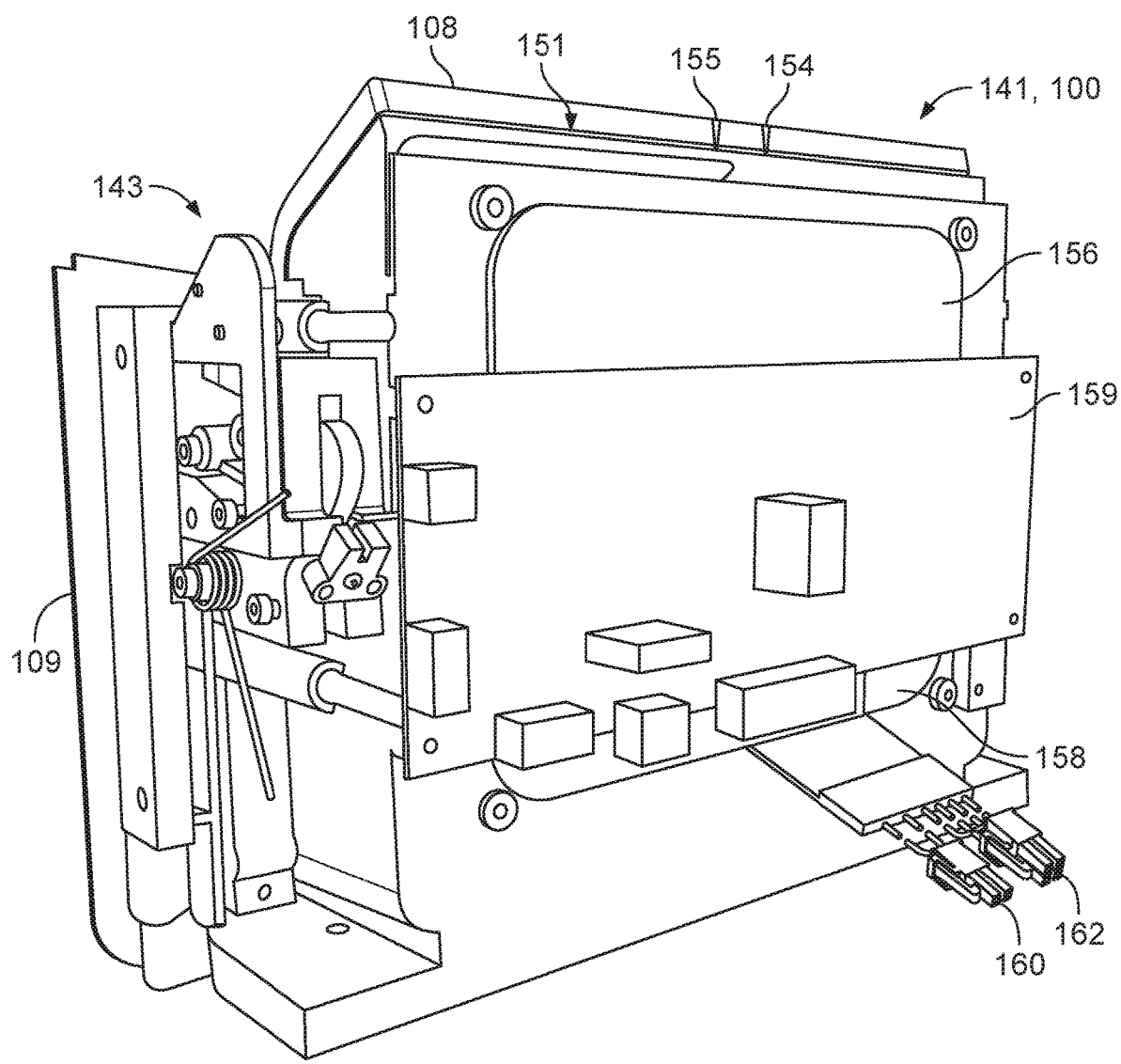
FIG. 10 is a rear perspective view of the front assembly of FIG. 9.
Figure 11:
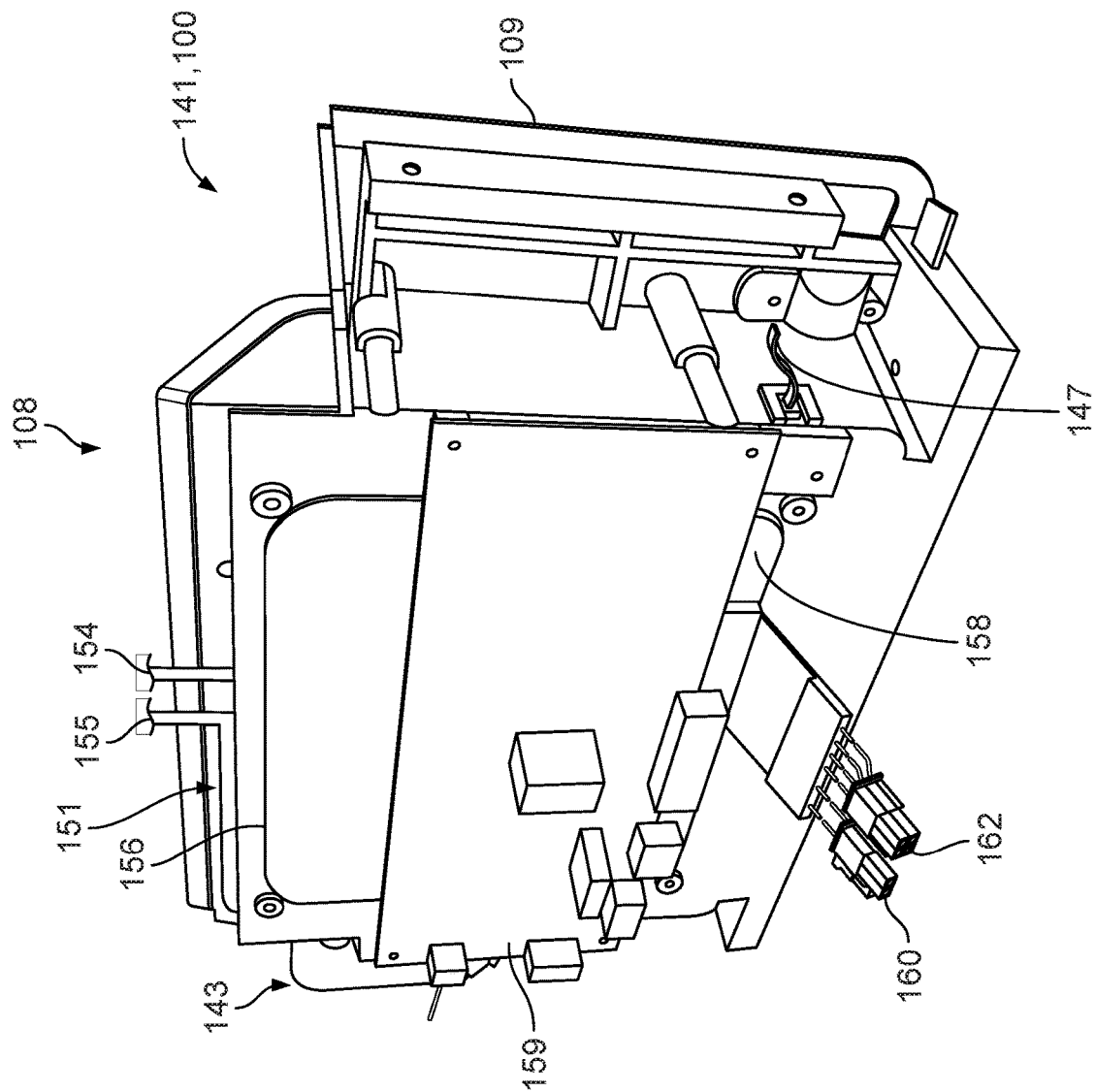
FIG. 11 is a rear perspective view of the front assembly of FIG. 9.
Figure 12:
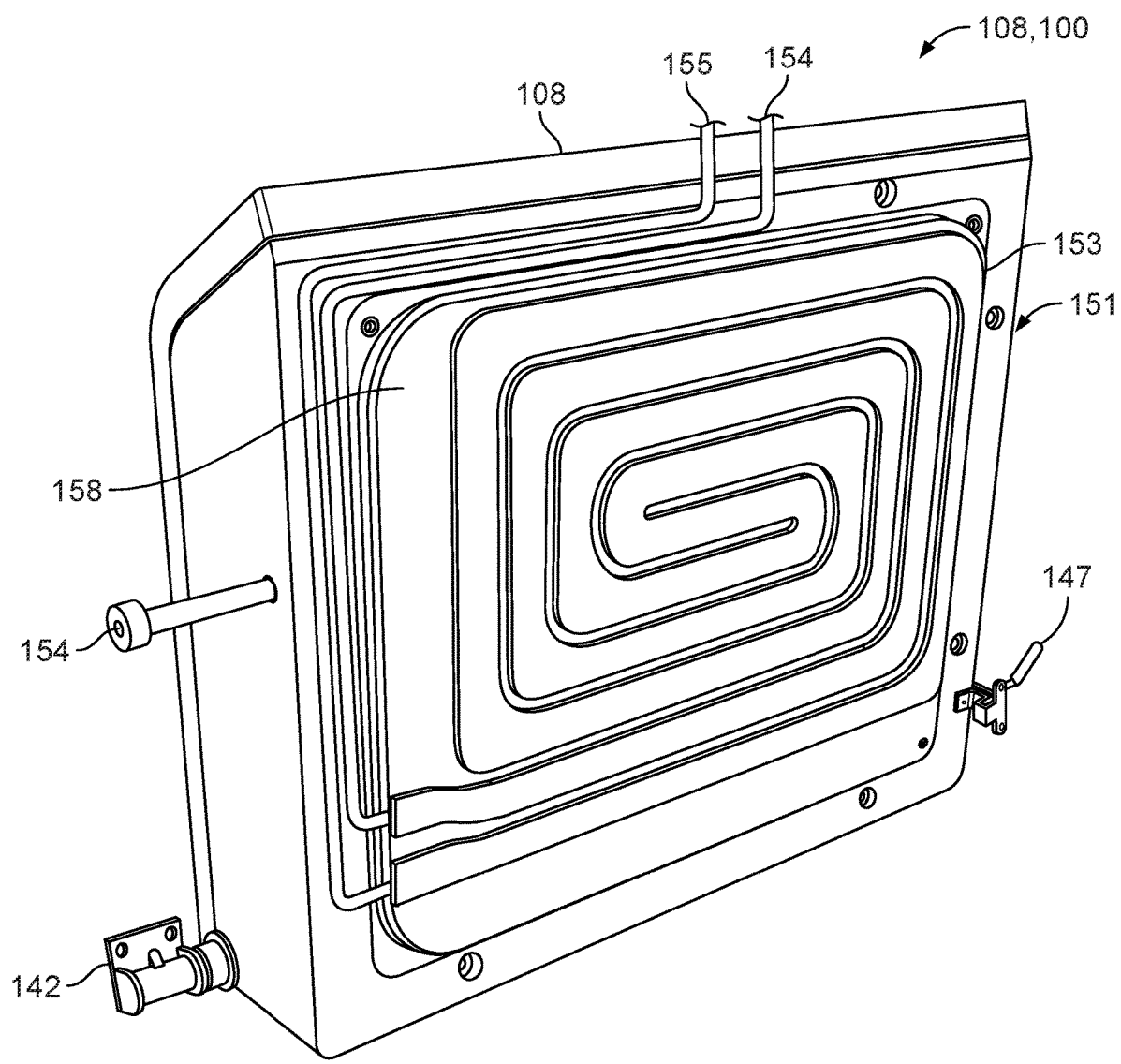
FIG. 12 is a rear perspective view of a heater bag of a door assembly of the front assembly of FIG. 9.

FIGS. 9-13 illustrate various views of a front assembly 141 of the fluid conditioning system 100. The front assembly 141 includes the door assembly 108 and the front panel 109 of the housing 101. The door assembly 108 is pivotable at hinges 142 with respect to the front panel 109 to allow loading of the heater bag 153 into the fluid conditioning system 100. The hinges 142 are friction hinges located along opposite sides of the door assembly 108, as shown in FIG. 12.

Figure 13:
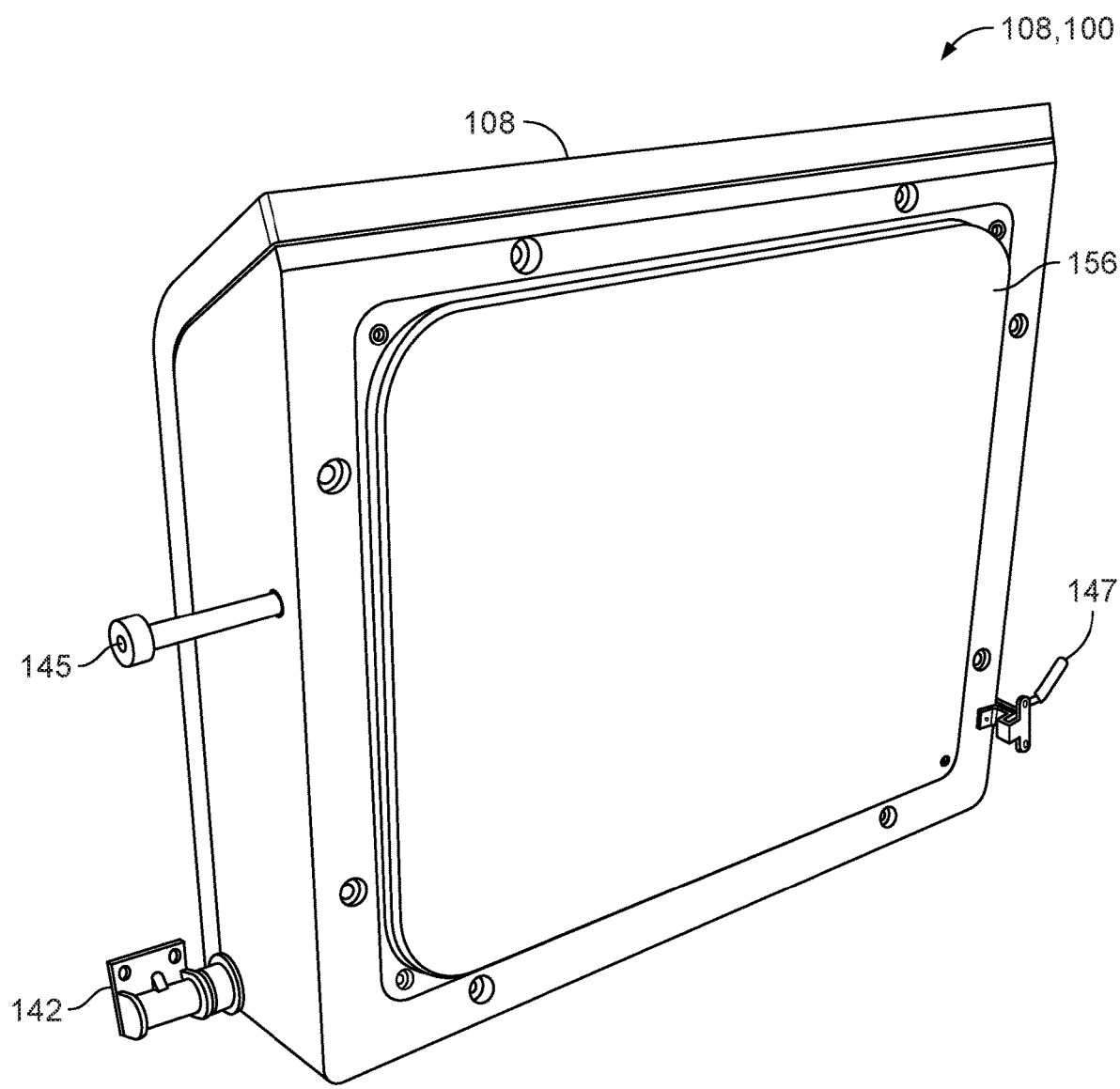
FIG. 13 is a rear perspective view of a heater plate of a door assembly of the front assembly of FIG. 9.

The front panel 109 carries a latch assembly 143 that cooperates with a button 144 carried by the upper panel 112 (shown in FIGS. 1-4) to releasably secure the door assembly 108 to the front panel 109 in a closed position. For example, depression of the button 144 adjusts the latch assembly 143 so that the door assembly 108 can be unlocked from a closed position and pivoted to an open position. The door assembly 108 can alternatively be pivoted inward from an open configuration until oppositely positioned screws 145 (e.g., shoulder screws, shown in FIG. 12) engage the latch assembly 131 to lock the door assembly 108 in the closed position. The latch assembly 131 has a contact switch for determining whether the door assembly 108 is open or closed. Referring particularly to FIGS. 11 and 13, the door assembly 108 includes an optical switch 147 that indicates whether or not the heater bag is inserted. In some embodiments, the fluid conditioning system 100 may be inoperable when the door assembly 108 is open.

Figure 9:
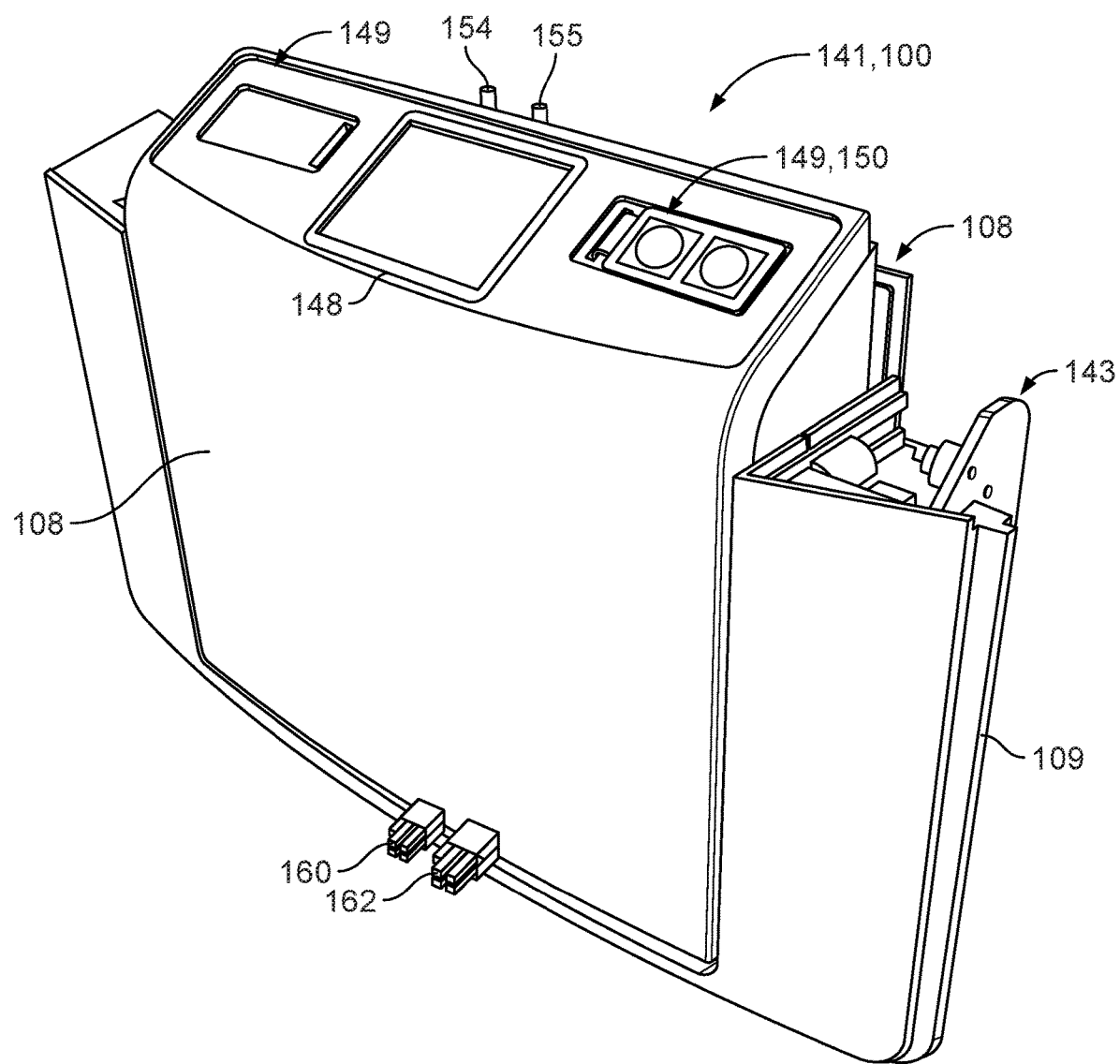
FIG. 9 is a perspective view of a front assembly of the fluid conditioning system of FIG. 1.

Referring particularly to FIG. 9, the door assembly 108 supports a display screen 148 (e.g., a touchscreen display) on which graphical user interfaces (GUIs) can be displayed and two control panels 149 that can each be equipped with selectors 150 (e.g., buttons) for providing inputs at the GUIs to operate the fluid conditioning system 100. Example parameters and processes that may be controlled by a user via the display screen 148 using the selectors 150 include starting and stopping a treatment, initiating a drain cycle, changing a flowrate, initiating a priming stage of a fluid conditioning cycle, initiating system preparation to start a fluid conditioning cycle, adjusting a temperature according to patient comfort, confirming correct placement of the fluid cassette 102, or confirming correct placement of fluid lines that interface with the pumps 103, 104.

Referring to FIGS. 10-13, the front assembly 141 includes components of a heater assembly 151 that is designed to regulate fluid temperatures of dialysate transported along the fluid pathways of the fluid cassette 102. Referring particularly to FIG. 12, the heater assembly 151 includes a heater bag 153 that is equipped with an input connection 154 and an output connection 155 that can interface with the fluid cassette 102 for allowing dialysate to circulate through the heater bag 153 to be warmed. The heater bag 153 is formed as a plastic channel that has a generally flat, collapsed shape when empty, that inflates upon filling with fluid, and that transfers heat from an exterior surface to dialysate flowing through the heater bag 153.

Figure 14:
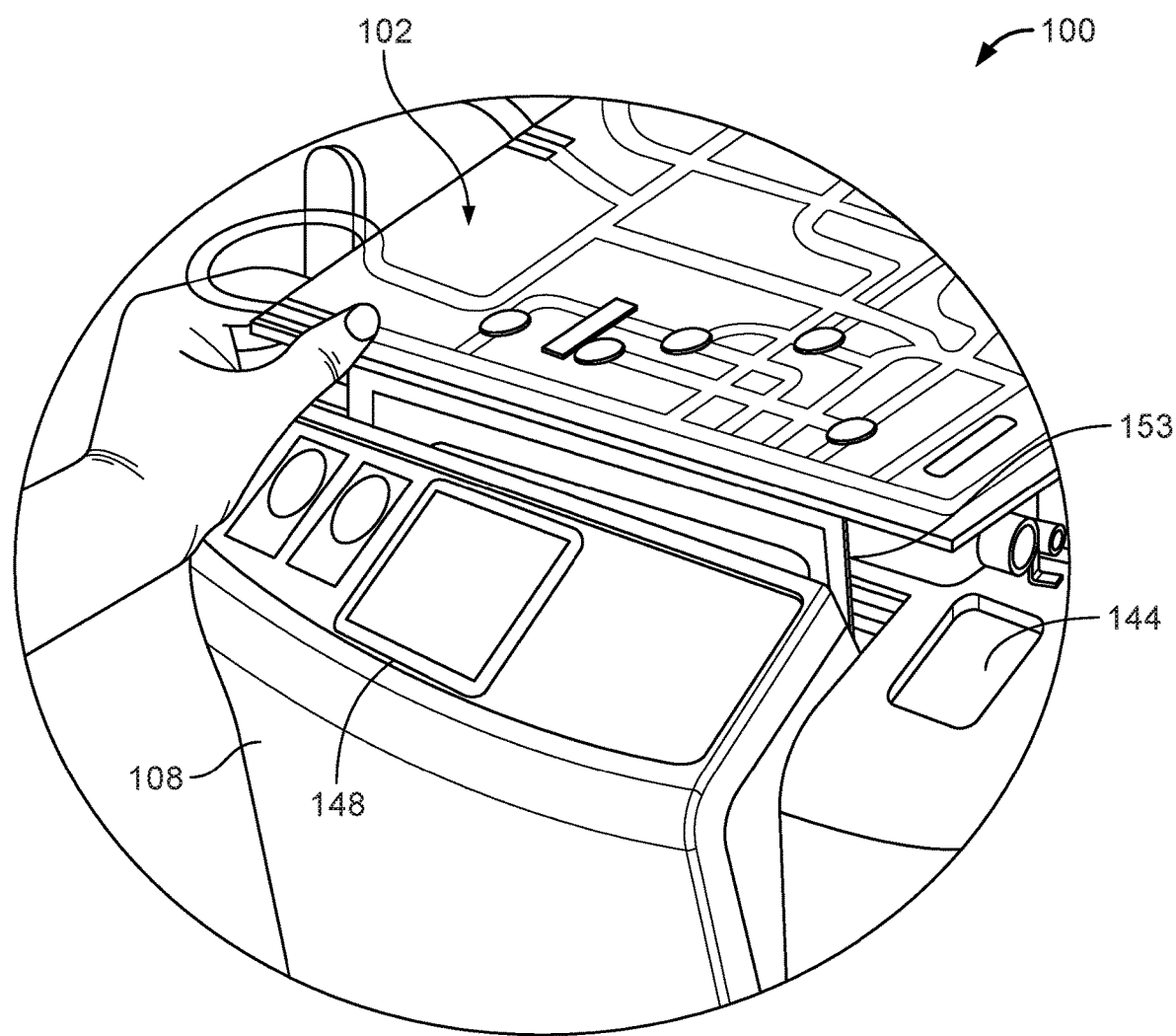
FIG. 14 is a perspective view illustrating installation of the heater bag of FIG. 12 and a fluid cassette of the fluid conditioning system of FIG. 1.

Referring particularly to FIG. 13, the heater assembly 151 further includes two plates 156 (e.g., aluminum plates) that position and support the heater bag 153 and that are heated for transferring heat to fluid within the heater bag 153. Referring particularly to FIG. 14, the heater bag 153 can be slid between the two heater plates 156 (not visible in FIG. 14) within the door assembly 108 when the door assembly 108 is in the open configuration. Referring particularly to FIGS. 10-12, the heater assembly 151 further includes one or more heating elements (for example, resistive type heating elements that are not shown) by which fluid in the heater bag 153 can be warmed and two insulation pads 158 disposed on opposite sides of the heater bag 153. The one or more heating elements are carried by or otherwise attached to one or both of the plates. The heater assembly 151 also includes a circuit board 159 that provides electronics for operating the heater assembly 151, a feed line 160 for each heating pad 156 that provides power, and thermocouple connections 162 for determining a temperature of the respective heating plates 156.

Figure 15:
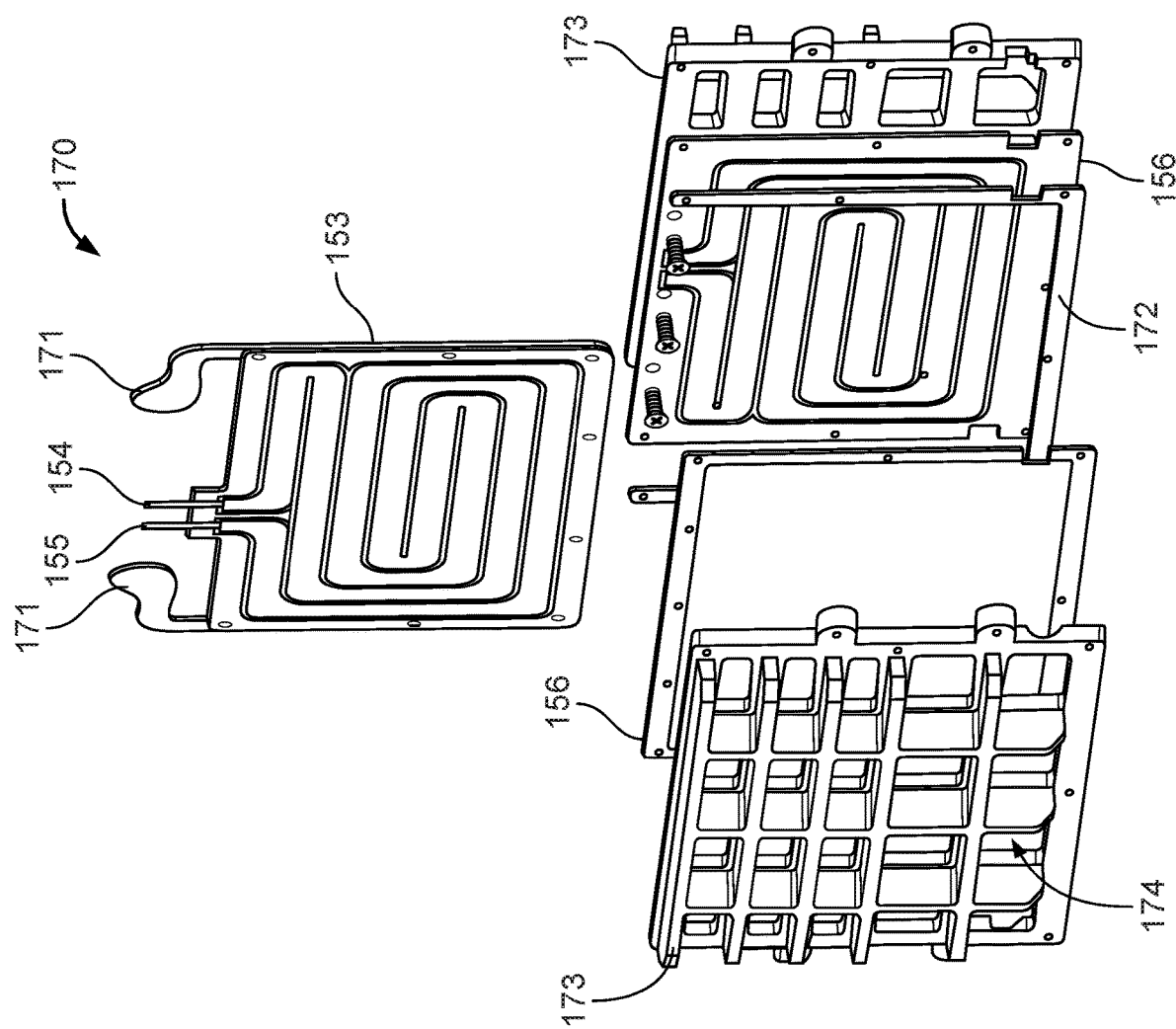
FIG. 15 is a perspective view of the fluid cassette of FIG. 14, along with the heater bag of FIG. 12.
Figure 16:
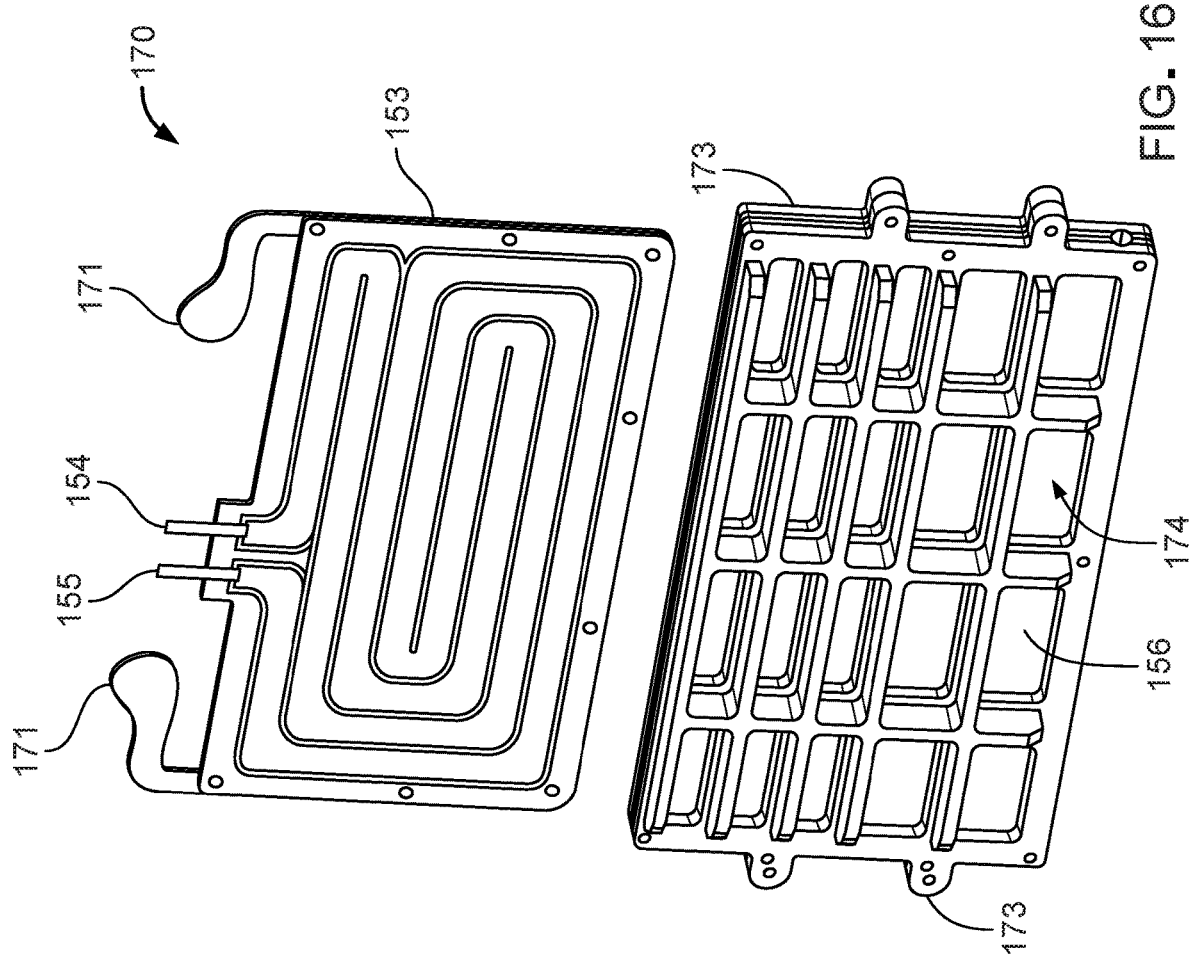
FIG. 16 is a full exploded perspective view of an embodiment of a heater assembly that may be included within the fluid conditioning system of FIG. 1.

FIGS. 15 and 16 illustrate another embodiment of a heater assembly 170 that may be included in the fluid conditioning system 100 instead of the heater assembly 151. The heater assembly 170 is similar in construction and function to the heater assembly 151 and accordingly includes the heater bag 153 sandwiched between the two heater plates 156. The heater assembly 170 further includes two handles 171 attached to the heater bag 153 for easy placement of the heater bag 153, a u-shaped heater frame 172 that supports the heater bag 153, and two support members 173 of a generally matrix construction that support the heater plates 156. The support members 173 further serve to insulate the heater bag 153 and the heater plates 156 from surrounding components via air gaps 174 defined by the matrix construction that are disposed between the heater plates 156 and such components.

Figure 17:
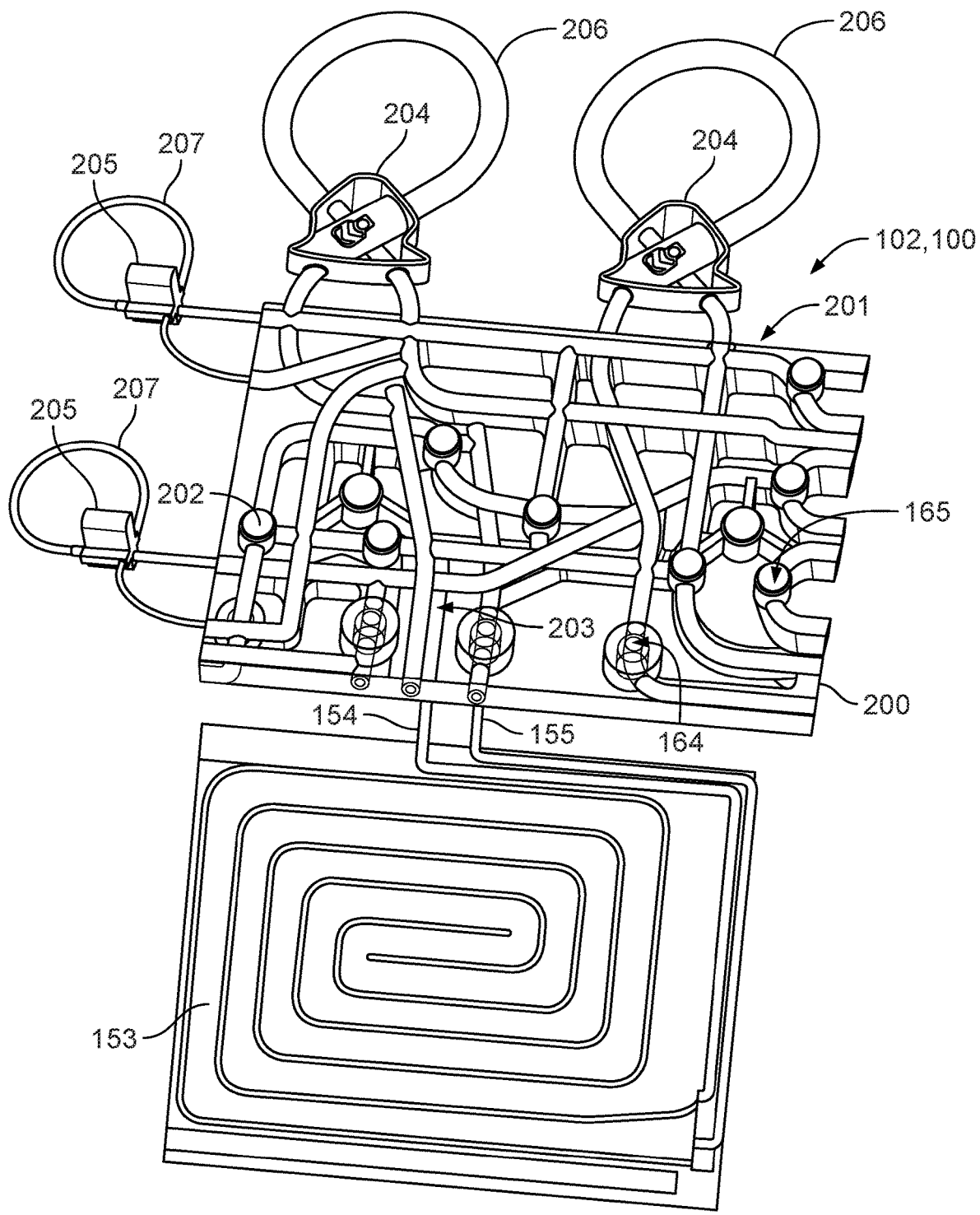
FIG. 17 is a partially exploded perspective view of the heater assembly of FIG. 16.

Referring to FIG. 17, the fluid cassette 102 is a single-use, disposable cartridge that includes a housing 200, multiple fluid lines 201 arranged within the housing 200, multiple valves 202 positioned along the fluid lines 201, two conductivity sensors 203 positioned along the fluid lines 201, an ammonia sensor 165 positioned along the fluid lines 201 for cooperation with the ammonia detector 121, two fluid line connectors (e.g., pump segment clips) 204, and two fluid line connectors (e.g., pump segment clips) 205. The fluid lines 201 cooperate with the heater bag 153 and a dialysis system to form a fluid circuit 350 for carrying out a fluid conditioning cycle. For example, the fluid lines 201 include ports to which the input and output connections 154, 155 of the heater bag 153 can be connected for providing fluid communication between the fluid lines 201 and the heater bag 153. The fluid line connectors 204 locate fluid line segments 206 about the high-capacity pumps 103, and the fluid line connectors 205 locate fluid line segments 207 about the low-capacity pumps 104. The fluid cassette 102 also includes additional fluid lines that extend from the fluid cassette 102 to various fluid containers, as illustrated in FIG. 19.

The valves 202 are three-way valves by which two alternative fluid pathways can be selected by a control system of the fluid conditioning system 100. Lower portions of the valves 202 are formed to engage with the coupling members 131 of the actuators 125 for movement of the valves 202. Example types of valves 202 that may be included in the fluid cassette 102 include rotary valves, push-pull valves, sliding valves, and shuttle valves.

Figure 18:
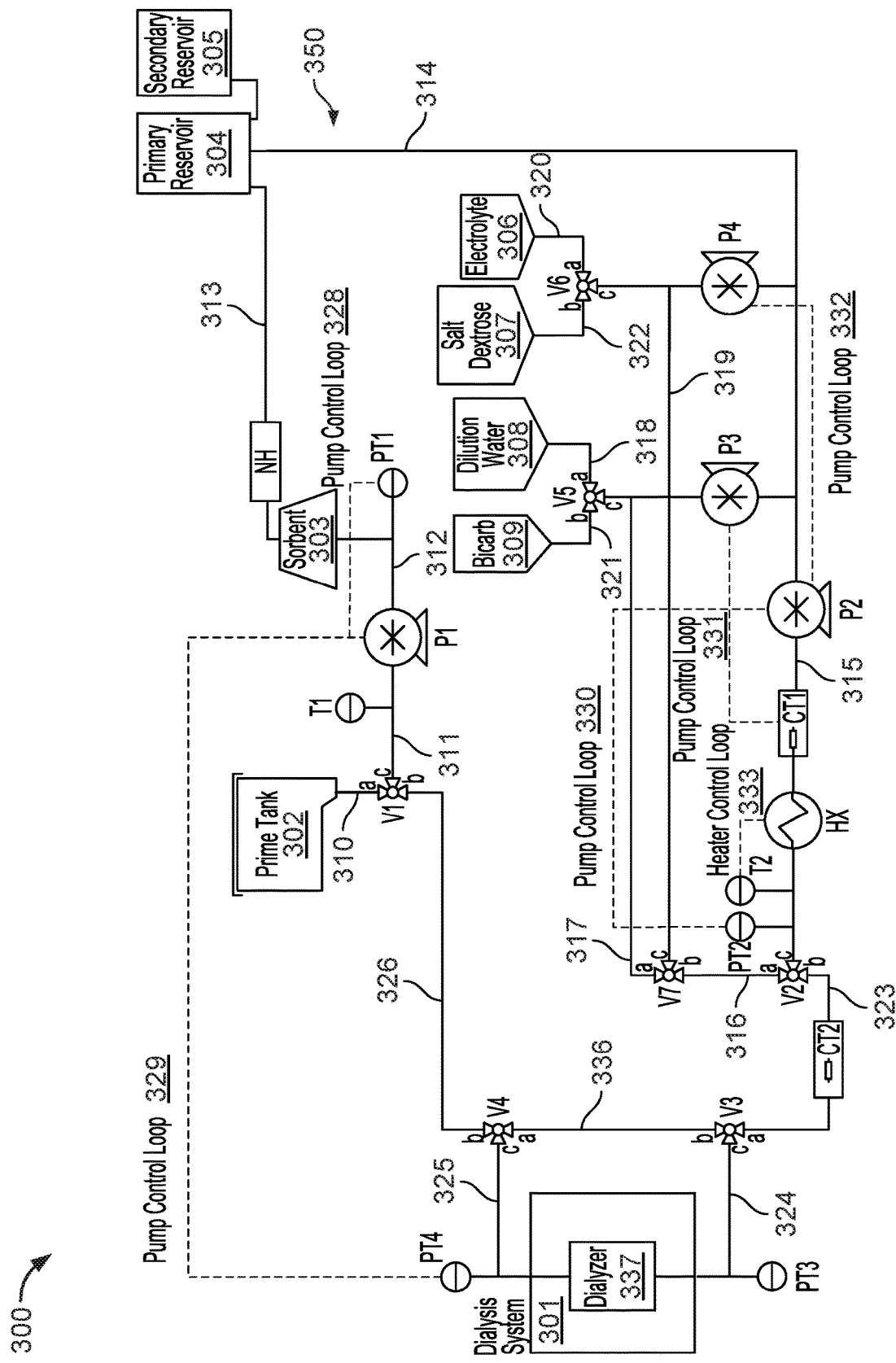
FIG. 18 provides an operational diagram by which the fluid conditioning system of FIG. 1 can cooperate with a dialysis system to form a fluid circuit for carrying out the fluid conditioning cycle.
Figure 19:
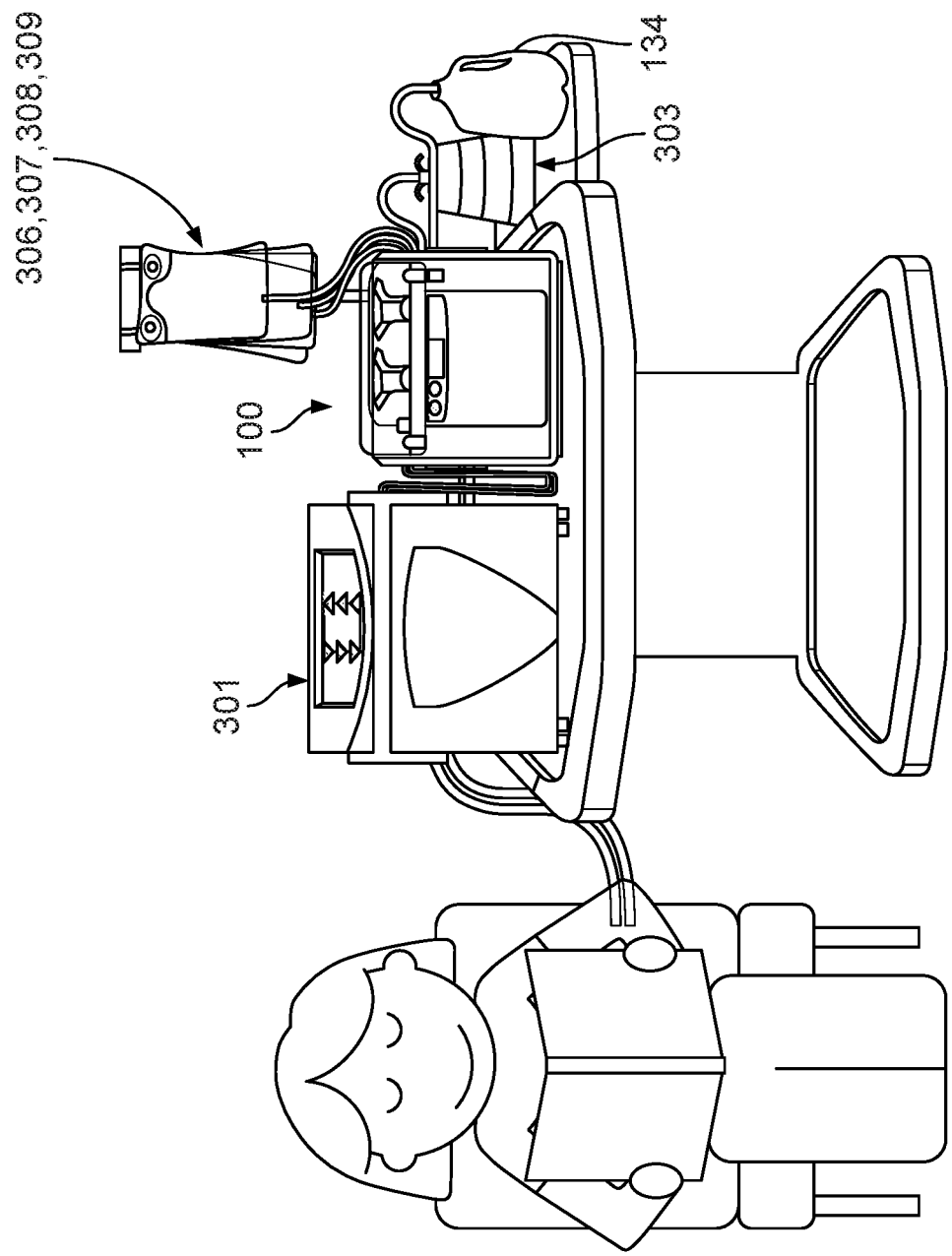
FIG. 19 illustrates an example setup of the fluid conditioning system of FIG. 1 with the dialysis system of FIG. 16.

FIG. 18 illustrates an operational diagram 300 by which the fluid conditioning system 100 can cooperate with a dialyzer 337 of a dialysis system 301 to form the fluid circuit 350 (indicated by solids lines) for carrying out a fluid conditioning cycle, while FIG. 19 illustrates an example setup of the fluid conditioning system 100 with the dialysis system 301. Example types of dialysis systems 301 that may be coupled to the fluid conditioning system 100 include HD systems, PD systems, HF systems, and HDF systems. The fluid circuit 350 incorporates components of the fluid cassette 102, as well as various other components of the fluid conditioning system 100.

For example, in addition to the components discussed above with respect to FIGS. 1-17, the fluid conditioning system 100 also includes a control system 161 (e.g., including the circuit boards 135, 159, as well as additional circuit boards for sensor circuitry) for controlling various operations of the fluid conditioning system 100 and several other, peripheral components positioned along the fluid circuit 350. These components include a prime tank 302 for collecting water to produce dialysate (e.g., sometimes referred to as dialysis fluid), a sorbent cartridge 303 for filtering tap water to provide purified water suitable for creating dialysate and for cleansing dialysate exiting the dialysis system 301, a primary reservoir 304 for collecting fluid (e.g., unconditioned water or dialysate) exiting the sorbent cartridge 303, a secondary reservoir 305 for collecting fluid that exceeds a capacity of the primary reservoir 304, a bag 306 for containing an electrolyte solution, a bag 307 for containing a salt-dextrose (SD) solution, a bag 308 for containing dilution water (DW), and a bag 309 for containing a bicarbonate (BC) solution that are positioned along the fluid flow path arrangement 300.

The bags 306, 307, 309 are pre-loaded with appropriate amounts of dry chemicals that can be dissolved in water to produce the electrolyte solution, the salt-dextrose solution, and the bicarbonate solution. Each bag 306, 307, 309 includes a nozzle that is designed to increase a velocity of a fluid flow entering the bag 306, 307, 309 and to create turbulence needed for adequate mixing and dissolution of the dry chemicals in water.

Table 1 lists approximate capacities of the various fluid-containing components of the fluid conditioning system 100.

TABLE 1

Capacities of fluid-containing components of the fluid conditioning system 100.

| Component | Capacity (mL) |
|---|---|
| Prime Tank (302) | 8,000 |
| Primary Reservoir (304) | 7,500 |
| Secondary Reservoir (305) | 4,500 |
| Electrolyte Bag (306) | 500 |
| Salt/Dextrose Bag (307) | 160 |
| Dilution Water Bag (308) | 4,000 |
| Bicarbonate Bag (309) | 1,000 |

The three-way valves 202 of the fluid cassette 102 are indicated as V1-V7 in the fluid circuit 350. Each valve includes three fluid ports (a), (b), (c) by which a flow path in the valve can be adjusted. A valve may be referred to as closed when two or three of its ports are closed and may be referred to as open when two or three of its ports are open. The valves include a prime valve V1, a dissolution valve V2, a bypass out valve V3, a bypass in valve V4, a BC/DW valve V5, an S/D/Electrolyte valve V6, and a fluid selector valve V7 The fluid lines 201 of the fluid cassette 102 will be referenced individually further below with respect to an operation of the fluid conditioning system 100. The high-capacity pumps 103 and the low-capacity pump 104 of the fluid conditioning system 100 are indicated respectively as P1, P2 and P3, P4 in the fluid circuit 350. The pumps include a cassette-in pump P1, a dialysate pump P2, a conductivity control pump P3, and an electrolyte/salt-dextrose pump P4. Table 2 lists approximate operational (e.g., fluid flow rate) ranges of the pumps P1-P4.

TABLE 2

Operational ranges of pumps of the fluid conditioning system 100.

| Pump | Operational Range (mL/min) |
|---|---|
| P1 | 20-600 |
| P2 | 20-600 |
| P3 | 0.5-90 |
| P4 | 0.5-90 |

The heater assembly 151 and the ammonia sensor 165 of the fluid conditioning system 100 are respectively indicated as a heat exchanger HX and an ammonia sensor NH in the fluid circuit 350. The conductivity sensors 203 of the fluid cassette 102 are indicated as a conductivity sensor CT1 associated with a fluid temperature upstream of the heat exchanger HX and a conductivity sensor CT2 associated with a fluid temperature downstream of the heat exchanger HX. In addition to having a capability to measure fluid conductivity, conductivity sensors CT1 and CT2 also have a capability to measure fluid temperature. Given that conductivity changes with temperature, the temperatures measured by the conductivity sensors CT1 and CT2 may, in some implementations, be used to correct conductivity values measured by the conductivity sensors CT1 and CT2 to provide temperature-compensated conductivity measurements. In some implementations, a fluid temperature measured by the conductivity sensor CT2 may also provide a safety check on a final temperature of dialysate that exits the fluid conditioning system 100 to flow into the dialysis system 303. The temperature sensors 120 of the fluid conditioning system 100 are indicated as a cassette-in temperature sensor T1 and a heat exchanger temperature sensor T2 in the fluid circuit 350. The pressure transducers 119 of the fluid conditioning system 100 are indicated as pressure transducers PT1, PT2, PT3, and PT4 in the fluid circuit 350.

The fluid conditioning system 100 can be operated in multiple stages to cooperate with the dialysis system 301 (e.g., with the dialyzer 337) for carrying out a fluid conditioning cycle in which a dialysis treatment is administered to a patient via the dialysis system 301. For example, the fluid conditioning cycle includes a priming stage, an infusion stage, and a treatment stage. The fluid conditioning cycle typically has a total duration of about 135 min to about 300 min.

Figure 20:
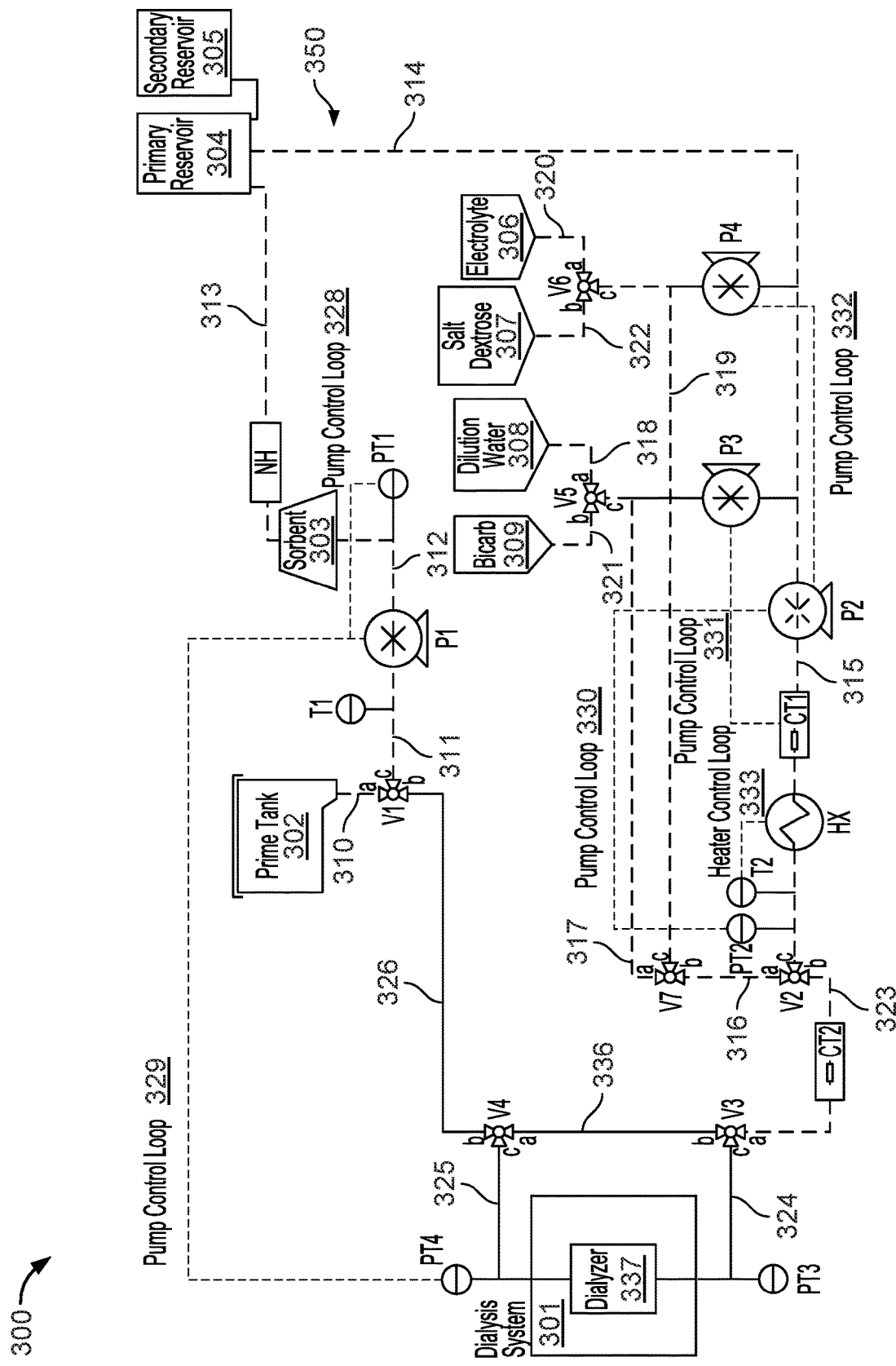
FIG. 20 illustrates a fluid flow path (indicated by highlighted fluid lines) of a priming stage of the fluid conditioning cycle carried out via the fluid circuit of FIG. 16.

FIG. 20 illustrates operation of the fluid conditioning system 100 during the priming stage, in which an initial volume of water is drawn into the fluid circuit 350 for subsequent creation of dialysate. At the beginning of the priming stage, the prime tank 302 is filled to about 7.6 L with water (e.g., tap water, bottled water, reverse osmosis water, distilled water, or drinking water) from a water source (e.g., a container 134 of water, shown in FIG. 19), pump P1 is turned on, and heat exchanger HX is turned on. The water is pumped by pump P1 from the prime tank 302 into a fluid line 310, through ports (a) and (c) of valve V1, into a fluid line 311, past temperature sensor T1, and into pump P1. At this stage of operation, pump P1 pumps water at a flow rate in a range of about 200 mL/min to about 600 mL/min, and heat exchanger HX is powered to maintain a fluid temperature at a set point in a range of about 15° C. to about 42° C.

If temperature sensor T1 detects a water temperature of greater than about 42° C., then a message is displayed on the display screen 148 to advise a user that the water temperature is too warm, valve V1 is closed, and pump P1 is turned off to prevent additional water from entering the fluid circuit 350. If temperature sensor T1 detects a water temperature of less than or equal to about 42° C., then ports (a) and (c) of valve V1 remain open, and pump P1 pumps the water through a fluid line 312 into the sorbent cartridge 303, into a fluid line 313, past ammonia sensor NH, and into the primary reservoir 304. At this stage of operation, the sorbent cartridge 303 purifies the water circulating in the fluid circuit 350, such that the water meets or exceeds water quality standards for drinking water as set by the Environmental Protection Agency (EPA) and water quality standards for hemodialysis water as set by the Association for the Advancement of Medical Instrumentation (AAMI) standard.

Once the primary reservoir 304 collects about 100 mL to about 500 mL of water, then pump P2 is turned on and pumps water into a fluid line 314, through pump P2, into a fluid line 315, past conductivity sensor CT1, and past the heat exchanger HX1, which heats the water in the fluid line 315 to the set point temperature. Pump P2 is controlled to pump water at a flow rate that is about equal to the flow rate at which water is pumped by pump P1. Water moves from the fluid line 315 through ports (c) and (a) of valve V2, into a fluid line 316, through ports (b) and (a) of valve V7, into a fluid line 317, through ports (c) and (a) of valve V5, into a fluid line 318, and further into the bag 308 until the bag 308 is filled to about 3.5 L to about 4.0 L with water (e.g., dilution water). Next, ports (a) and (c) of valve V5 are closed, port (a) of valve V7 is closed, and port (c) of valve V7 is opened such that the pump P2 pumps water into a fluid line 319, through ports (c) and (a) of valve V6, into a fluid line 320, and further into the bag 306 until the bag 306 is filled to capacity with water to produce the electrolyte solution. Ports (a) and (c) of valve V6 are closed, port (c) of valve V7 is closed, port (a) of valve V7 is reopened, and ports (b) and (c) of valve V5 are opened. Pump P2 then pumps water into the fluid line 317, through ports (c) and (b) of valve V5, into a fluid line 321, and further into the bag 309 until the bag 309 is filled to capacity with water to produce the bicarbonate solution.

At this point in the priming stage, the set point temperature of the heat exchanger HX is increased to a range of about 31° C. to about 39° C. (e.g., where 39° C. is the maximum temperature achievable by heat exchanger HX), and the flow rate of pump P2 is reduced to a value within a range of about 100 mL/min to about 300 mL/min to increase an exposure time of the water within the heat exchanger HX for achieving the higher set point temperature. Ports (b) and (c) of valve V5 are closed, port (a) of valve V7 is closed, port (c) of valve V7 is opened, and ports (b) and (c) of valve V6 are opened. Accordingly, pump P2 pumps water into the fluid line 319, though ports (c) and (b) of valve V6, into a fluid line 322, and further into the bag 307 until the bag 307 is filled to capacity to produce the salt-dextrose solution. The higher set point temperature of heat exchanger HX facilitates dissolution of the salt-dextrose substance with the water flowing into the bag 309. At this point during the fluid conditioning cycle, the priming stage concludes, the prime tank 302 has substantially emptied, the pumps P1, P2 are turned off and the infusion stage can begin. The priming stage typically lasts a duration of about 10 min to about 30 min (e.g., about 20 min).

Figure 21:
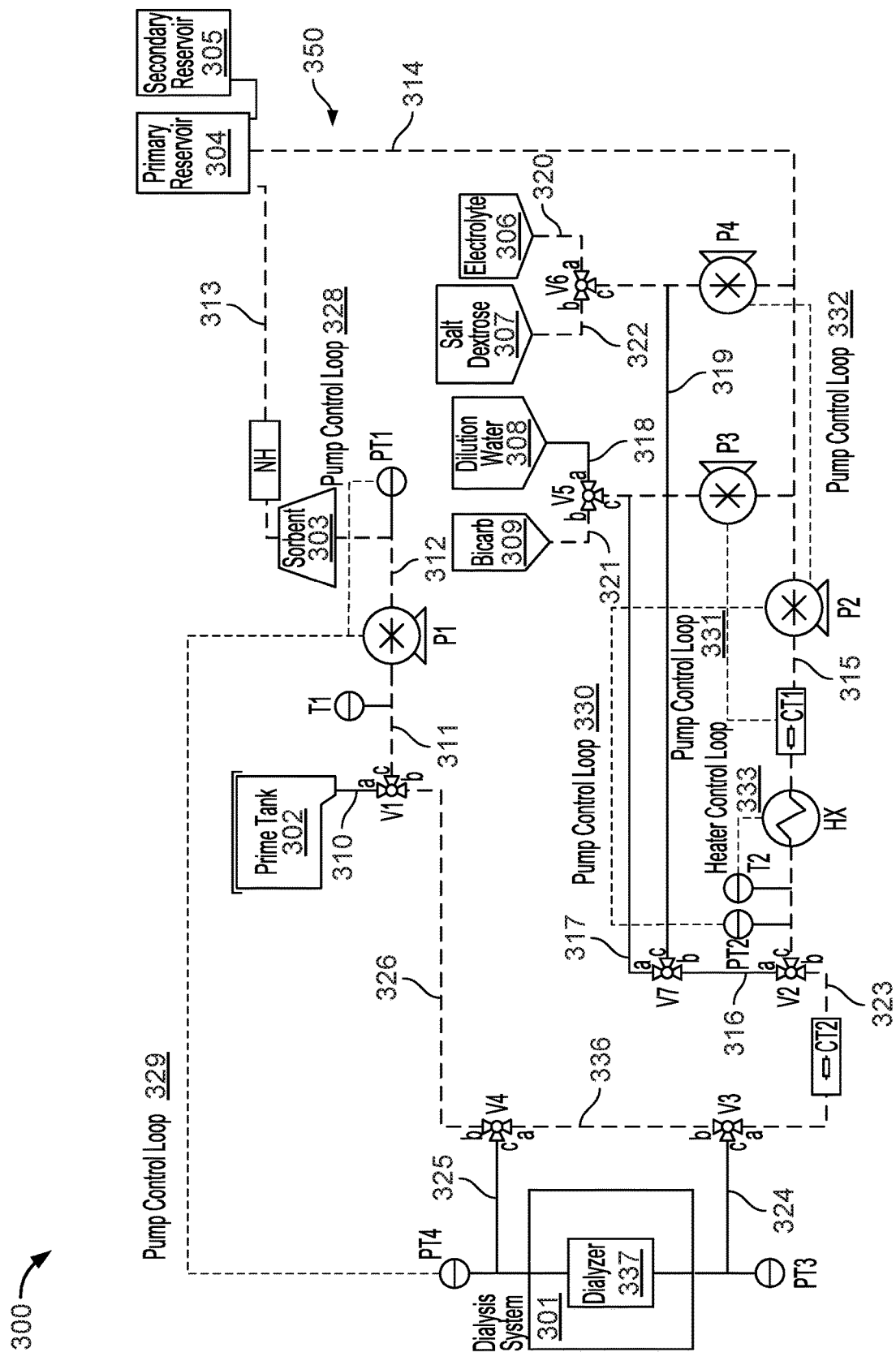
FIG. 21 illustrates a fluid flow path (indicated by highlighted fluid lines) of an infusion stage of the fluid conditioning cycle carried out via the fluid circuit of FIG. 16.

FIG. 21 illustrates operation of the fluid conditioning system 100 during the infusion stage, in which bicarbonate, salt, and dextrose are added to the water in the fluid circuit 350 to produce dialysate. In particular, bicarbonate, salt, and dextrose are added to the water in a controlled manner (e.g., under flow rate control) until the salt and dextrose reach physiologically acceptable concentrations and until the bicarbonate yields a physiologically acceptable fluid conductivity and fluid pH. During the infusion stage, heat exchanger HX is powered to maintain a fluid temperature at a set point in a range of about 35° C. to about 39° C.

At the beginning of the infusion stage, valve V7 is closed, port (a) of valve V2 closes, port (b) of valve V2 opens, ports (a) and (b) of both valves V3 and V4 open, port (b) of valve V1 opens, port (a) of valve V1 closes, ports (b) and (c) of valve V6 remain open, and ports (b) and (c) of valve V5 open. Pumps P1, P2 immediately turn on to pump water at a flow rate in a range of about 300 mL/min to about 600 mL/min within the fluid circuit 350. At the same time, pumps P3 and P4 are turned on. Pump P3 pumps bicarbonate solution out of the bag 309 at a flow rate of about 10 mL/min to about 100 mL/min, into the fluid line 317, through the pump P3, and into the fluid line 314. Pump P4 pumps salt-dextrose solution out of the bag 307 at a variable flow rate into the fluid line 319, through pump P4, and into the fluid line 314. The flow rate at which P4 initially pumps fluid is in a range of about 1 mL/min to about 100 mL/min. The flow rate is gradually stepped down by a factor of 2 at periodic time increments of about 1 min. The flow rates of pumps P3 and P4 are set to completely add the infusion volume respectively of the BC solution and the SD solution over a single revolution around the fluid circuit 350. Accordingly, the flow rates of pumps P3 and P4 depend on the flow rates of pumps P1 and P2 during the infusion stage. For example, if the flow rates of pumps P1 and P2 are set to 200 mL/min, then the flow rates of pumps P3 and P4 will be relatively slow. Conversely, if the flow rates of pumps P1 and P2 are set to 600 mL/min, then the flow rates of pumps P3 and P4 will be relatively fast.

Once the bag 307 empties of the salt-dextrose solution, port (b) of valve V6 closes, and port (a) of valve V6 opens to allow pump P4 to pump the electrolyte solution out of the bag 306 at a flow rate of about 0.5 mL/min to about 5 mL/min into the fluid line 314. Once the electrolyte solution reaches valve V3, the infusion stage concludes, and the treatment stage can begin. However, if the treatment stage does not begin immediately, the fluid conditioning system 100 can be operated to continue to circulate dialysate around the fluid circuit 350 through fluid lines 311, 312, 313, 314, 315, 323, 336, 326 or to allow the dialysate to remain static (e.g., without circulation) until the treatment stage begins. The infusing stage typically lasts a duration of about 5 min to about 6 min.

Figure 22:
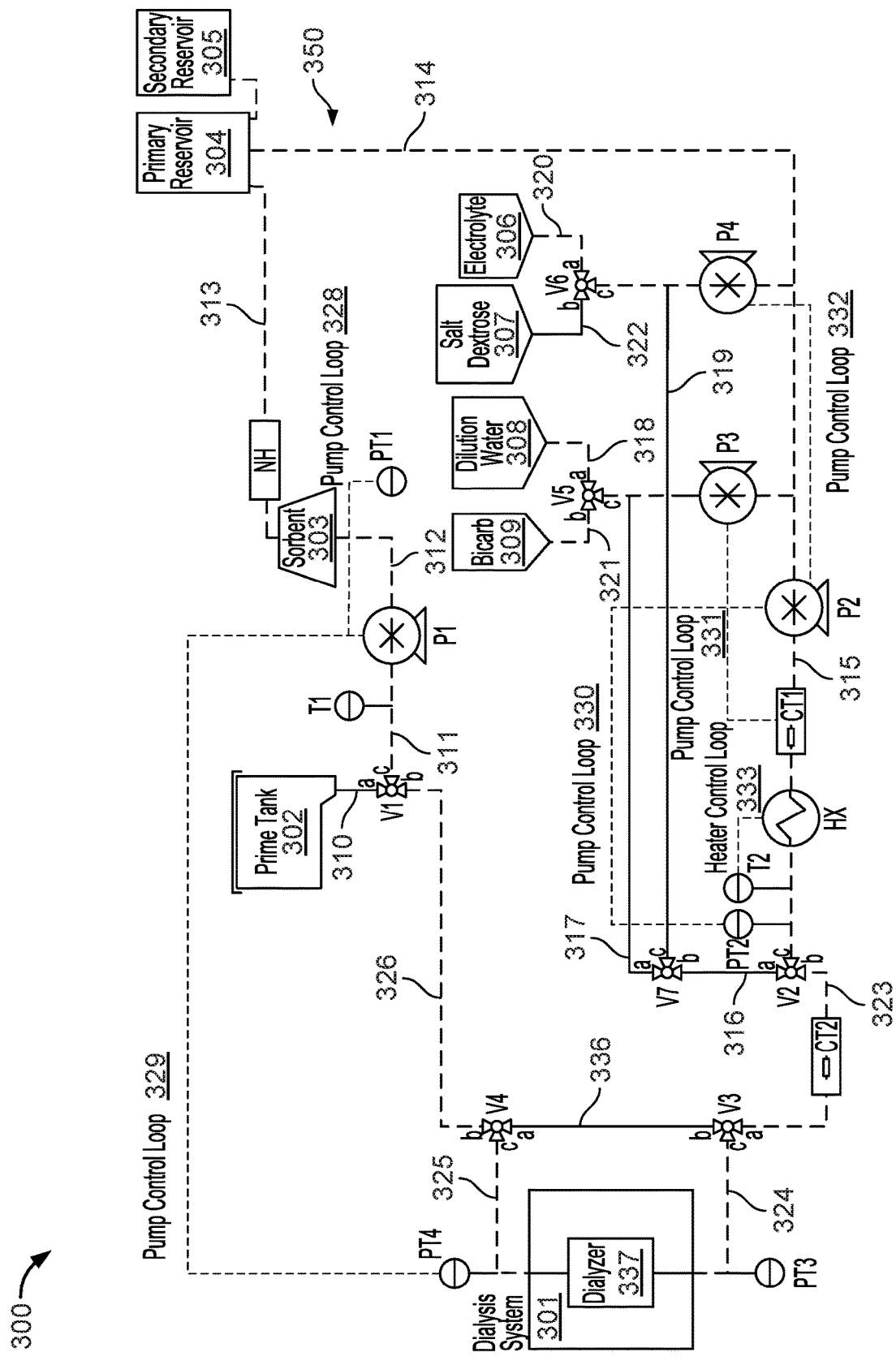
FIG. 22 illustrates a fluid flow path (indicated by highlighted fluid lines) of a treatment stage of the fluid conditioning cycle carried out via the fluid circuit of FIG. 16.

FIG. 22 illustrates operation of the fluid conditioning system 100 during the treatment stage, in which bicarbonate, salt, and dextrose are added to the water in the fluid circuit 350 to produce dialysate. The treatment stage includes a first phase in which bicarbonate solution is used to regulate a conductivity of the dialysate and a second phase in which dilution water is used to regulate a conductivity of the dialysate. Pumps P1, P2 pump dialysate at a flow rate in a range of about 200 mL/min to about 600 mL/min. The set point temperature of heat exchanger HX is maintained at a physiologically acceptable temperature in an acceptable range of about 35° C. to about 39° C. (e.g., about 37° C.), as specifically selected by a user of the fluid conditioning system 100 to suit patient comfort. At any point during the treatment stage, if the dialysate fluid temperature measured at CT2 is outside of a range of about 35° C. to about 42° C., then the fluid conditioning system 100 will enter a bypass mode in which dialysate will flow through fluid line 336 to bypass flow through the dialysis system 301 via fluid lines 324, 325. While the fluid conditioning system 100 is operating in the bypass mode, a message will be displayed on the display screen 148 indicating that the fluid temperature is too low or too high. The fluid conditioning system 100 will remain in bypass mode until the fluid temperature stabilizes within the acceptable range.

During the first phase of the treatment stage, port (b) of valve V3 is closed, port (c) of valve V3 is opened to allow pump P2 to pump "fresh" dialysate (e.g., cleaned, conditioned dialysate) through a fluid line 324 and into the dialysis system 301, port (a) of valve V4 is closed, and port (c) of valve V4 is opened to allow pump P1 to pump "spent" dialysate (e.g., contaminated dialysate) through a fluid line 325 out of the dialysis system 301 and further into a fluid line 326. Accordingly, a bypass fluid line 336 that extends between valves V3, V4 is closed. During the treatment stage, spent dialysate is infused with ultra-filtrate from the patient's blood within the dialysis system 301. The ultra-filtrate carries toxic substances, such as urea, all of the small water-soluble uremic toxins, and other toxic substances (e.g., guanidosuccinic acid, methylguanidine, 1-methyladenosine, 1-methylinosine, N2,N2-dimethylguanosine, pseudouridine, arab(in)itol, mannitol, α-N-acetylarginine, orotidine, oxalate, guanidine, erythritol, creatine, orotic acid, phenylacetylglutamine, creatinine, myoinositol, γ-guanidinobutyric acid, β-guanidinopropionic acid, symmetric dimethyl-arginine (SDMA), asymmetric dimethyl-arginine (ADMA), sorbitol, uridine, and xanthosine).

From the fluid line 326, the spent dialysate is pumped through ports (b) and (c) of valve V1, the fluid line 311, pump P1, the fluid line 312, and into the sorbent cartridge 303. Within the sorbent cartridge 303, the toxic substances are removed from (e.g., filtered out of) the spent dialysate to produce "regenerated" dialysate (e.g., cleaned, unconditioned dialysate) that flows out of the sorbent cartridge 303 and into the fluid line 313, past the ammonia sensor NH, and into the primary reservoir 304. In some cases, a volume of the regenerated dialysate within the primary reservoir 304 exceeds a capacity of the primary reservoir 304 and therefore flows through a fluid line 327 into the secondary reservoir 305, which remains in fluid communication with the primary reservoir 304 throughout the treatment stage. Pump P2 pumps regenerated dialysate out of the primary reservoir 304, into the fluid line 314, and into pump P2. While the regenerated dialysate exiting the sorbent cartridge 303 has been stripped of toxic substances that were absorbed from the patient's blood in the dialysis system 301, the regenerated dialysate must be further conditioned to meet acceptable physiological properties before being circulated back into the dialyzer 337 of the dialysis system 301 as fresh dialysate.

Accordingly, pump P4 continues to pump the electrolyte solution out of the bag 306 and into the fluid line 320, through ports (a) and (c) of valve V6, into an upper segment of the fluid line 319, through pump P4, and into the fluid line 314 at a flow rate that depends on (e.g., is a fraction of) the flow rate at which pump P2 pumps dialysate. Thus, pumps P2, P4 together form a closed pump control loop 332 that governs the flow rate at which pump P4 pumps the electrolyte solution, which is in a range of about 0.5 mL/min to about 5 mL/min. Furthermore, pump P3 continues to pump either the bicarbonate solution out of the bag 309 or the dilution water out of the bag 308, through port (c) of valve V5, into an upper segment of the fluid line 317, through pump P3, and into the fluid line 314 to further condition the dialysate.

As the dialysate passes through pump P2 and conductivity sensor CT1, the conductivity sensor CT1 detects a conductivity of the dialysate. Based on continuous measurements of the conductivity of the dialysate, either the bicarbonate solution or the dilution water will be continuously selected for addition to the dialysate through port (c) of valve V5, and the flow rate at which pump P3 pumps dialysate will be continuously adjusted to maintain a conductivity of the dialysate within a physiologically acceptable range of 13.5 mS/cm to 14.2 mS/cm. Generally, as a difference between the measured conductivity and an acceptable conductivity increases, the flow rate at which the pump P3 pumps fluid increases. Accordingly, as the difference between the measured conductivity and the acceptable conductivity decreases, the flow rate at which the pump P3 pumps fluid decreases. In this manner, the conductivity meter CT1 and the pump P3 together form a closed pump control loop 331 that regulates a flow rate at which the pump P3 pumps fluid. If the conductivity of the dialysate is too low during the first phase of the treatment stage, then bicarbonate solution is infused into the dialysate to raise the conductivity.

After passing the conductivity sensor CT1, the dialysate flows past the heat exchanger HX and temperature sensor T2. Based on a fluid temperature detected by temperature sensor T2, a power level of the heat exchanger HX will be adjusted to maintain the temperature of the dialysate at the set point temperature of the heat exchanger HX. In this way, temperature sensor T2 and heat exchanger HX form a closed heater control loop 333. The dialysate flows from the fluid line 315 through ports (c) and (b) of valve V2 into the fluid line 323 and past conductivity sensor CT2. As the dialysate passes conductivity sensor CT2, conductivity sensor CT2 performs a second check (e.g., downstream of heat exchanger HX) to detect a conductivity of the dialysate.

If the conductivity of the dialysate is outside of the acceptable range (e.g., either too low or too high), but within a predetermined range (e.g., that is broader than the acceptable range), then a safety system in electrical communication with the conductivity sensor will adjust a flow rate of infusion of the bicarbonate solution or the dilution water to achieve a conductivity within the acceptable range. If the conductivity level of the dialysate is outside of the predetermined physiologically safe range, then, in some implementations, the fluid conditioning system 100 will attempt to restore the safe fluid parameters and continue the treatment. For example, valves V3 and V4 will adjust to direct fluid through the bypass fluid line 336 and close fluid lines 324, 325 until a time at which the conductivity has again stably reached a physiologically safe range, at which time valves V3, V4 will adjust to close the bypass fluid line 336 and direct fluid to and from the dialysis system 301 via fluid lines 324, 325. In some implementations, a user may also be instructed to check that fluid levels of the bicarbonate solution and the dilution water are non-zero upon return of the conductivity to a physiologically safe range.

Over time, the sorbent cartridge 303 changes a composition of the regenerated dialysate exiting the sorbent cartridge 303 during the first phase of the treatment stage (e.g., an early, initial phase in which the patient's blood is initially circulated through the dialysis machine 301). For example, during the first phase of the treatment stage, levels of toxic substances within the spent dialysate are relatively high. The sorbent cartridge 303 converts urea into ammonium and captures the ammonium within one or more filtration layers within the sorbent cartridge 303 to remove the ammonium from the dialysate. While the filtration layers capture the ammonium, the filtration layers release sodium cations and other cations into the dialysate via cation exchange, which increases the conductivity and/or decreases the pH of the regenerated dialysate exiting the sorbent cartridge 303.

Over the course of the first phase of the treatment stage, spent dialysate entering the sorbent cartridge 303 contains fewer toxic substances (e.g., as uremic toxins are removed from the patient's blood), and the sorbent cartridge 303 releases more sodium cations. Therefore, the conductivity of the dialysate exiting the sorbent cartridge 303 gradually increases over time. Once the conductivity of the dialysate reaches a predetermined value in a range of about 13.8 mS/cm to about 14.0 mS/cm, the first phase of the treatment stage in which bicarbonate is used to regulate the conductivity of the dialysate concludes, and the second phase of the treatment stage begins.

During the second (e.g., later, final) phase of the treatment stage, bicarbonate is no longer used to regulate (e.g., increase) the conductivity of the dialysate, and dilution water is the sole substance at valve V5 that is used to regulate (e.g., decrease) the conductivity of the dialysate until the end of the treatment stage (e.g., the end of the second phase). Accordingly, port (b) of valve V5 is closed, while port (a) of valve V5 is opened. If the conductivity of the dialysate is too high during the second phase of the treatment stage, then dilution water is infused into the dialysate to lower the conductivity of the dialysate.

Over the course of the second phase of the treatment stage, an amount of ammonium captured in the sorbent cartridge 303 increases, such that a capacity of the sorbent cartridge 303 to absorb additional ammonium gradually decreases, and a level of ammonia (e.g., generated by the ammonium) within the regenerated dialysate eventually increases, once the capacity of the sorbent to adsorb ammonium is exhausted. The ammonia sensor NH detects the level of ammonia within the regenerated dialysate at a location downstream of the sorbent cartridge 303.

The treatment stage (e.g., including both the first and second phases) typically lasts a duration of about 120 min to about 300 min. For example, 240 minutes (e.g., 4 hours) is a standard duration that typically achieves adequate treatment for the vast majority of patients. Furthermore, most treatment stages will end after four hours without reaching a threshold ammonium concentration of 2 mg/dL (e.g., without ever approaching exhaustion of the filtering capabilities of the sorbent cartridge 303). The fluid conditioning system 100 will sound an audio alert signifying that the treatment completed successfully and that the patient can disconnect himself or herself from the dialyzer 337. However, if the ammonium level in the dialysate (e.g., as detected by the ammonia sensor NH) indicates that the sorbent cartridge 303 is no longer absorbing enough ammonium from the spent dialysate to maintain the ammonium level at or below an acceptable value of about 2 mg/dL prior to the standard treatment duration, then the treatment stage will conclude prematurely. Such conditions may occur occasionally for larger patients that have very high blood urea nitrogen (BUN) levels.

Once the treatment stage concludes, the fluid circuit 350 can be drained of spent dialysate, and the spent dialysate can be disposed of as waste. In some examples, the bags 306, 307, 308, 309 and the various fluid lines can be manually removed and discarded while still containing dialysate. In some examples, the patient may disconnect from the dialysis system 301 and drain the fluid lines 323, 326 to a waste receptacle to empty the various components of the fluid conditioning system 100. In some examples, the fluid conditioning system 100 may be operated to run either or both of pumps P1, P2 in a forward direction or a reverse direction to drain any of the bags 306, 307, 308, 309, the sorbent cartridge 303, the prime tank 302, the primary reservoir 304, and the secondary reservoir 305. In some examples, the fluid conditioning system 100 may be operated to run pumps P4 and P3 in a forward direction to drain the bags 306, 307 and 308, 309. In some examples, such operation of pumps P4, P3 may be carried out based on readings at conductivity meter CT1. For example, upon detection of a sufficiently low threshold conductivity, the electrolyte bag 306 may be assumed to have been emptied, such that a next bag or fluid line can be drained.

Throughout the fluid conditioning cycle, pressure transducers PT1, PT2, PT3, PT4 detect fluid pressures to regulate pump flow rates. For example, during all stages (e.g., the priming, infusion, and treatment stages) of the fluid conditioning cycle, pressure transducer PT1 forms a closed pump control loop 328 with pump P1 by detecting a fluid pressure of the dialysate within the fluid line 312 (e.g., located downstream of pump P1) and providing a feedback signal to pump P1 indicative of the fluid pressure. Based on the fluid pressure of the dialysate, an angular speed (e.g., an RPM level) of pump P1 is adjusted to maintain the flow rate within a desired range. During the treatment stage of the fluid conditioning cycle, pressure transducer PT4 forms an additional closed pump control loop 329 with pump P1 by detecting a fluid pressure of the dialysate exiting the dialysis system 301 (e.g., upstream of pump P1) and providing a forward signal to pump P1 indicative of the fluid pressure. Based on the fluid pressure of the dialysate, the angular speed of pump P1 is adjusted to closely match the flow rate at pump P1 with that of the dialysate exiting the dialysis system 301. Accordingly, the fluid pressure of the dialysate within the fluid line 312 (e.g., downstream of pump P1) is at least in part affected by the fluid pressure of the dialysate exiting the dialysis system 301 (e.g., upstream of pump P1).

Similarly, during all stages (e.g., the priming, infusion, and treatment stages) of the fluid conditioning cycle, pressure transducer PT2 forms a closed pump control loop 330 with pump P2 by detecting a fluid pressure of the dialysate within the fluid line 315 (e.g., located downstream of pump P2) and providing a feedback signal to pump P2 indicative of the fluid pressure. Based on the fluid pressure of the dialysate, an angular speed of pump P2 is adjusted to maintain the flow rate within a desired range. During the treatment stage of the fluid conditioning cycle, the flow rate at which pump P3 pumps fluid is regulated by a feedback signal from conductivity meter CT1 to form the pump control loop 331, and the flow rate at which pump P4 pumps the electrolyte solution is regulated by a feedback signal from pump P2 to form the pump control loop 332, as discussed above.

During all stages of the fluid conditioning cycle, pressure transducers PT3 and PT4 detect operation of the dialyzer 337. If measurements at pressure transducers PT3 and PT4 indicate that there is no fluid flow through the dialyzer 337, then the fluid conditioning system 100 will enter the bypass mode to flow dialysate through fluid line 336 and to avoid delivering dialysate to the dialysis system 301 via fluid lines 324, 325.

Figure 23:
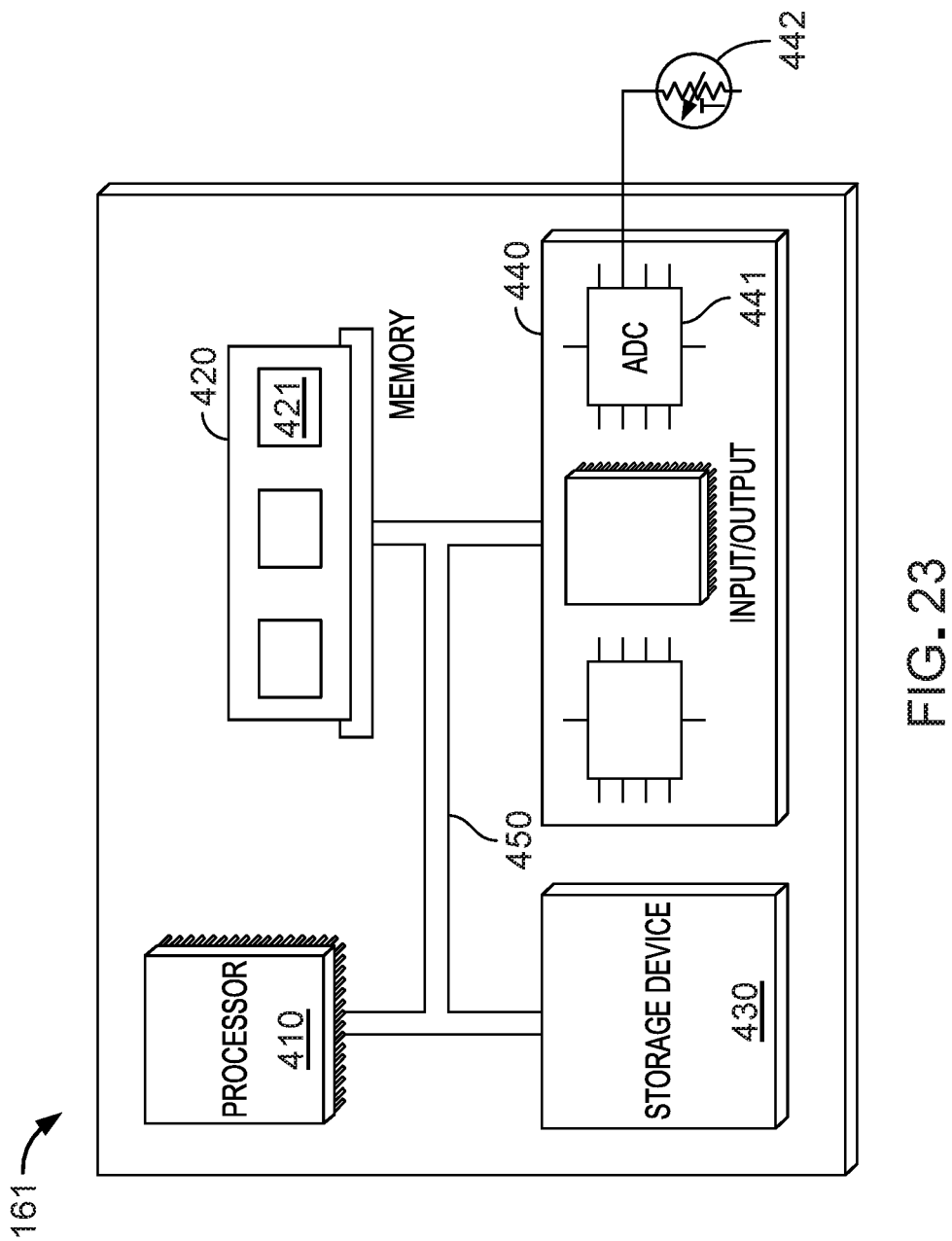
FIG. 23 provides a block diagram of a control system of the fluid conditioning system of FIG. 1.

FIG. 23 provides a block diagram of the control system 161. The control system 161 includes a processor 410, a memory 420, a storage device 430, and an input/output interface 440. In some embodiments, the control system 161 includes more than one processor 410, memory 420, storage device 430, and/or input/output interface 440. Each of the components 410, 420, 430, and 440 can be interconnected, for example, using a system bus 450. The processor 410 is capable of processing instructions for execution within the control system 161. The processor 410 can be a single-threaded processor, a multi-threaded processor, or a quantum computer. The processor 410 is capable of processing instructions stored in the memory 420 or on the storage device 430.

The memory 420 stores information within the control system 161. In some implementations, the memory 420 is a computer-readable medium. The memory 420 can, for example, be a volatile memory unit or a non-volatile memory unit. The storage device 430 is capable of providing mass storage for the control system 139. In some implementations, the storage device 430 is a non-transitory computer-readable medium. The storage device 430 can include, for example, a hard disk device, an optical disk device, a solid-state drive, a flash drive, magnetic tape, or some other large capacity storage device. The storage device 430 may alternatively be a cloud storage device, e.g., a logical storage device including multiple physical storage devices distributed on a network and accessed using a network.

The input/output interface 440 provides input/output operations for the control system 161. In some implementations, the input/output interface 440 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and display devices (e.g., the display screen 148). In some implementations, mobile computing devices, mobile communication devices, and other devices are used.

In some implementations, the input/output interface 440 includes at least one analog-to-digital converter 441. An analog-to-digital converter converts analog signals to digital signals, e.g., digital signals suitable for processing by the processor 410. In some implementations, one or more sensing elements are in communication with the analog-to-digital converter 441, as will be discussed in more detail below.

In some implementations, the control system 161 is a microcontroller. A microcontroller is a device that contains multiple elements of a computer system in a single electronics package. For example, the single electronics package could contain the processor 410, the memory 420, the storage device 430, and input/output interfaces 440.

FIGS. 24 and 25 provide block diagrams of a hardware system 500 and a software system 600 of the fluid conditioning system 100 that are provided by the control system 161. As shown in FIG. 24, the hardware system 500 is provided by a circuit board for generating GUIs for display on the display screen 148 and one or more circuit boards 135 for controlling the electromechanical peripheral components of the fluid conditioning system 100, and the various electromechanical peripheral components. The software system 600 can be broken down into an external view 610, an application layer 620, and a driver layer 630. The external view 610 includes user interfaces provided by the GUIs, lights, sounds, and debug ports. The application layer 620 includes business logic, and the driver layer 630 is configured to implement peripheral-specific code (e.g., communication protocols and stepper motor drivers).

Although the example control system 161, the example hardware system 500, and the example software system 600 have been described respectively in FIGS. 23-25, implementations of the subject matter and the functional operations described above can be implemented in other types of digital electronic circuitry, or in computer software, firmware, or hardware, including the structures disclosed in this specification and their structural equivalents, or in combinations of one or more of them.

Figure 26:
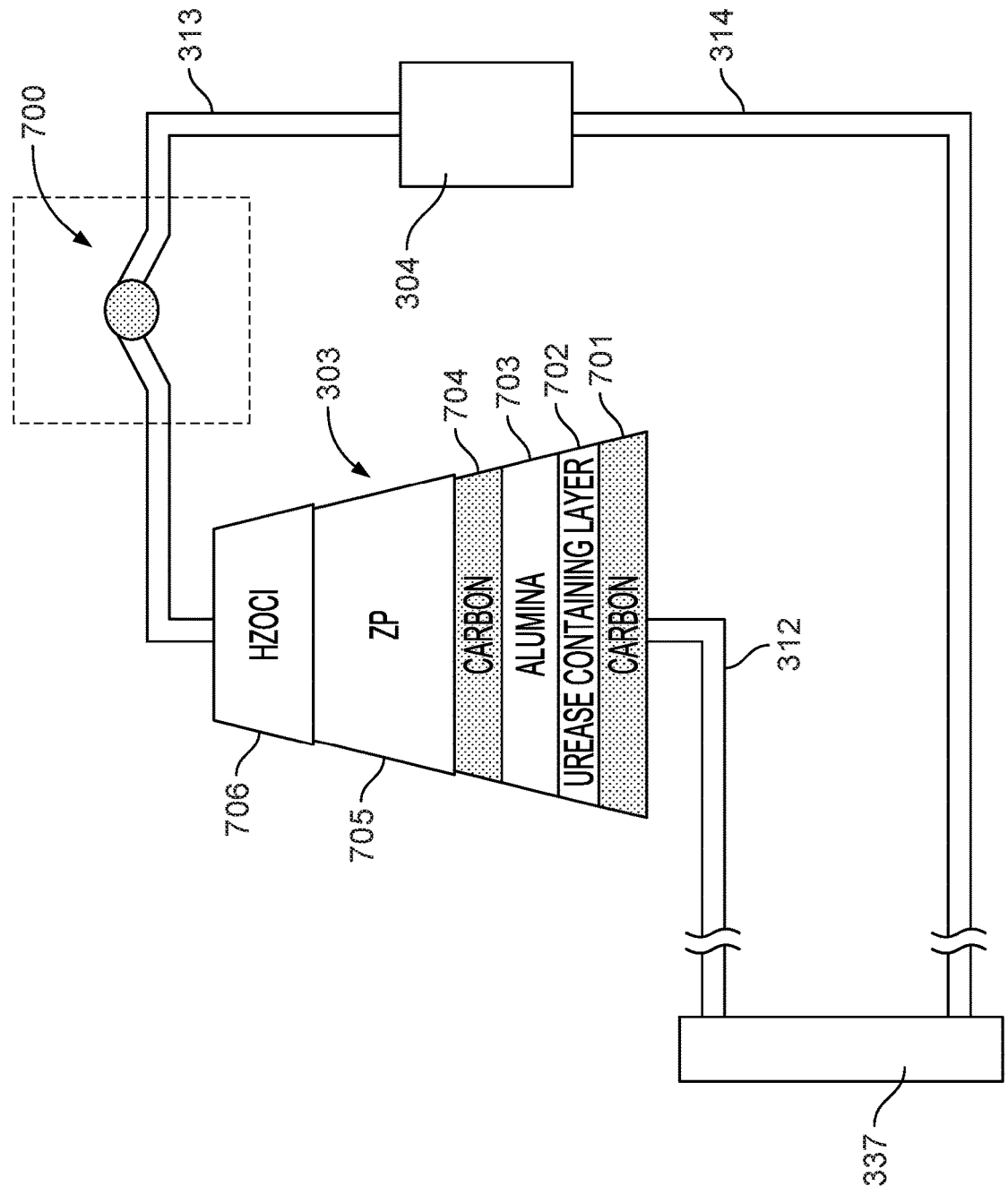
FIG. 26 shows a portion of the operational diagram of FIG. 18, including an ammonia detection system, a sorbent cartridge, and a primary reservoir of the fluid conditioning system of FIG. 1.
Figure 29:
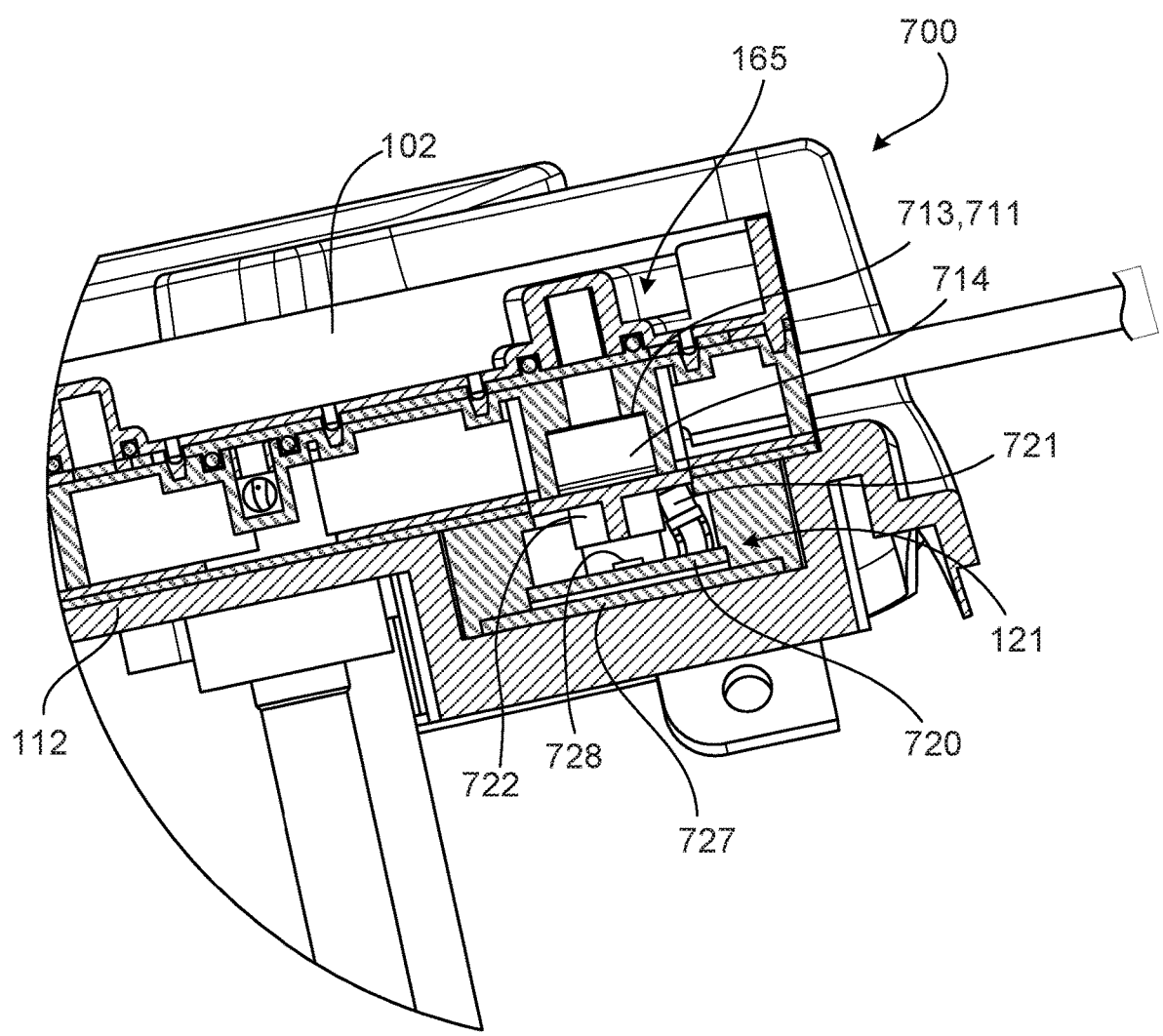
FIG. 29 is a cross-sectional view of the ammonia detection system of FIG. 26.

In some embodiments, the ammonia sensor 165 and the cooperating ammonia detector 121 together provide an ammonia detection system 700 of the fluid conditioning system 100, as illustrated in FIG. 26. As discussed above with respect to FIGS. 18 and 19, the sorbent cartridge 303 is designed to regenerate spent dialysate that circulates through the fluid circuit 350. The spent dialysate contains urea that has diffused across the dialyzer 337 from the patient's blood, and ammonium is produced within the dialysate as a result of urea decomposition within the sorbent cartridge 303. The sorbent cartridge 303 is therefore designed to remove ammonium as part of the process of regenerating the spent dialysate. Ammonium that is not removed from the dialysate within the sorbent cartridge 303 can generate ammonia within the circulating dialysate. Therefore, the ammonia detection system 700 is positioned downstream of the sorbent cartridge 303 (e.g., but upstream of the primary reservoir 304, shown in FIG. 18) for determining whether an ammonium level within the regenerated dialysate that exits the sorbent cartridge 303 is within an acceptable range.

As shown in FIG. 26, the sorbent cartridge 303 includes various layers that together regenerate the spent dialysate. For example, the sorbent cartridge 303 includes a first carbon layer 701, a urease layer 702, an alumina layer 703, a second, intermediate carbon layer 704, a zirconium phosphate (ZP) layer 705, and a Hydrous Zirconium Oxide with chloride counter ion (HZOCl) layer 706. The carbon layers 701, 703 adsorb heavy metals, chloramines, other contaminants that may be present in tap water, and many organic and middle molecule uremic solutes found in spent dialysate, such as creatinine and uric acid. The urease layer 702 decomposes the urea in the dialysate into ammonium (e.g., positively charged ammonium ions, $NH_4^+$) and bicarbonate. The alumina layer 703 immobilizes the urease enzyme and other proteins leaching out of the urease layer 702. The ZP layer 705 adsorbs ammonium (e.g., thereby removing ammonium from the circulating dialysate), and the HZOCl layer 706 adsorbs phosphates leaching out of the ZP layer 705 or from the patient through the dialyzer 337.

The ZP layer 705 has a fixed ammonium adsorption capacity. Therefore, if the ammonium adsorption capacity of the ZP layer 705 is exceeded during the treatment stage of a fluid conditioning cycle in which the dialysate is regenerated, then ammonium can begin to leak into dialysate that flows out of the sorbent cartridge 303. Ammonium, by itself, may not pose a direct health threat to the patient. However, the ammonium transferred to the patient (e.g., into the patient's blood) through the dialyzer 337 can generate ammonia (e.g., ammonia gas) either in the fluid circuit 350 or in the patient's blood, and ammonia is toxic above a certain threshold concentration (e.g., about 100 µg/dL). Depending on a pH and a temperature of the dialysate within the fluid circuit 350, trace amounts of ammonia gas are generated within the dialysate from the ammonium present in the dialysate. Therefore, the ammonia detection system 700 is positioned just downstream of sorbent cartridge 303 in order to identify ammonium leakage in the dialysate and thereby protect the patient from overexposure to ammonia.

Referring to FIGS. 26 and 27, the ammonia sensor 165 includes a connector body 707 that is assembled with the fluid line 313 of the fluid circuit 350 within the disposable fluid cassette 102. The ammonia sensor 165 further includes a sensor housing 709 positioned within a receptacle 708 of the connector body 707, a gas permeable membrane 711 positioned within the sensor housing 709, a snap ring 712 (e.g., an o-ring member) that locates and supports the membrane 711, a sensor 713 positioned adjacent the membrane 711, a lens 714 (e.g., a borosilicate lens) that closes an opening of the sensor housing 709, and a baffle 715 positioned within a vertical flow channel 716 of the connector body 707.

The sensor housing 709 is an opaque component that absorbs ambient light such that a predominant amount of light radiated towards the sensor 713 is provided by the ammonia detector 121, as will be discussed in more detail below. The sensor housing 709 has a generally cylindrical exterior shape for placement within the receptacle 708 of the connector body 707 and typically has an outer diameter of about 1.11 cm to about 1.36 cm. The sensor housing 709 may be made of polycarbonate or one or more other materials. The membrane 711 is permeable to ammonia gas vapors such that the vapors can pass through the membrane 711 to reach the sensor 713. The membrane 711 and the sensor 713 typically have a diameter of about 0.94 cm to about 1.08 cm (e.g., about 0.95 cm). The sensor 713 is provided as a layer of paper (e.g., cellulose paper) that is sandwiched between the membrane 711 and the lens 714. In some embodiments, the layer of paper is coated with bromocresol green at a concentration of about 500 ppm to about 1200 ppm (e.g., 1,000 ppm) and malonic acid at a concentration of about 500 ppm to about 1000 ppm (e.g., about 1,000 ppm). The sensor 713 typically has a thickness of about 0.15 mm to about 0.32 mm (e.g., about 0.24 mm).

Bromocresol green is an acid base indicator. In the presence of an acidic substance (e.g., with a pH less than about 3.4), bromocresol green forms a complex that has a yellow color, whereas in the presence of a relatively basic substance (e.g., with a pH greater than about 5.4), bromocresol green forms a complex that has a blue color. Since the sensor 713 is initially dipped in an acid (e.g., malonic acid), the sensor 713 initially has a yellow color. Ammonia is a base and therefore changes the color of the sensor 713 from yellow to blue upon contact with the sensor 713. Detection of such a color change at the sensor 713 may occur automatically at the cooperating ammonia detector 121, such that the dialysis treatment can be stopped in order to avoid exposing the patient to the toxic threshold concentration of ammonia.

Referring to FIGS. 27 and 28, the baffle 715 is a small plate that provides an obstruction to a flow of the circulating dialysate. For example, the baffle 715 is oriented perpendicular to a bulk flow direction 717 of the circulating dialysate within the vertical flow channel 716, which is positioned along a horizontal flow channel 710 of the connector body 707. The baffle 715 is designed to generate turbulence in the flow of dialysate to promote flow of any ammonia gas vapors within the dialysate upward along a sense direction 718 towards the membrane 711. The baffle 715 includes a relatively wide base 730 and a relatively narrow protrusion 732 that extends from the base 730 into an opening of the sensor housing 709 to define a planar flow area 734 along a perimeter of the protrusion 732 and an upper edge of the base 730.

The width of the base 730 is equal to an internal diameter of the vertical flow channel 716, such that the circulating dialysate is forced to flow up over the base 730 and through the flow area 734. The flow area 734 is the cross-sectional area defined between the protrusion 732 and adjacent inner surfaces of the sensor housing 709, the snap ring 712, and the membrane 711. Such a flow path increases a velocity of the dialysate through the flow area 734 since the flow area 734 is less than a cross-sectional area of the horizontal flow channel 710. The increased velocity generates turbulence in the circulating dialysate and therefore increases a rate at which ammonia gas vapors diffuse across the membrane 711 for early detection of ammonia within the dialysate, which is an indicator of ammonium leakage into the dialysate within the sorbent cartridge 303. The protrusion 732 reduces a distance between the flow path and the membrane 711, and the ammonia gas vapors diffuse across a clearance space 736 (e.g., a clearance volume) formed between the protrusion 732 and the membrane 711.

The base 730 of the baffle 715 and the vertical flow channel 716 typically have a diameter of about 0.5 cm to about 1.0 cm. The horizontal flow channel 710 typically has a diameter of about 0.5 cm to about 1.2 cm. The protrusion 732 of the baffle 715 typically has a width of about 0.5 cm to about 1.5 cm and a length of about 1.0 cm to about 1.8 cm. The baffle 715 typically has a total height of about 1.8 cm to about 2.8 cm and a thickness of about 0.13 cm to about 0.2 cm. In some embodiments, the annular cross-sectional flow area 734 falls within a range of about 70 mm$^2$ to about 90 mm$^2$ (e.g., about 80 mm$^2$). As the circulating dialysate flows through the flow area 734, ammonia gas vapors within the dialysate diffuse through the membrane 711 to the sensor 713, causing the sensor 713 to change from a yellow color to a blue color. Light reflected from the sensor 713 passes through the lens 714 towards the ammonia detector 121.

Referring to FIGS. 29-32, the ammonia detector 121 is positioned along the upper panel 112 (e.g., a durable, non-disposable component of the housing 101 of the fluid conditioning system 100, refer to FIGS. 6 and 7) in alignment with and beneath the ammonia sensor 165. The ammonia detector 121 operates according to principles of reflectance spectroscopy to detect changes in the color of the sensor 713. The ammonia detector 121 includes a housing 719 defining two beveled through-channels 723 at which the housing 719 can be secured to a supporting member, a printed circuit board (PCB) 727 attached to the housing 719, a light emitting diode (LED) 721 within a lateral opening 724 of the housing 719 that radiates light towards the lens 714 of the ammonia sensor 165, a detector 728 for receiving light reflected from the sensor 713, digital detector circuitry 720 (e.g., digital RGB detector circuitry) adjacent the detector 728 for processing signals received at and sent from the detector 728, a lens 722 (e.g., a borosilicate lens) within a central opening 725 of the housing 719 that focuses the reflected light onto the detector 728, and a connector 726 that places the PCB 727 in electrical communication with the control system 161 (refer to FIG. 23) of the fluid conditioning system 100.

The housing 719 is an opaque component that absorbs ambient light such that a predominant amount of light radiated towards the ammonia sensor 165 is provided by the LED 721. The LED 721 shines white, broadband light towards the ammonia sensor 165, where the light passes through the lens 714 and illuminates the sensor 713. The broadband light emitted by the LED 721 typically has wavelengths in a range of about 450 nm to about 750 nm. The lens 722 reduces a field of vision of the sensor 713 down to a narrow central region of the sensor 713 to further reduce effects of any ambient light that may be reflected by the sensor 713.

The detector 728 is a multi-chromatic band pass component (e.g., a Red-Green-Blue detector) that includes multiple channels that detect visible light of different colors reflected from the sensor 713. For example, the detector 728 includes a red channel 731 that detects visible red light with wavelengths in a range of about 630 nm to about 700 nm, a green channel 733 that detects green light with wavelengths in a range of about 530 nm to about 575 nm, a blue channel 735 that detects blue light with wavelengths in a range of about 450 nm to about 490 nm, and a broadband channel 737 that detects white light with wavelengths in a range of about 450 nm to about 750 nm. A normalized reference point is established for the red, green, and blue channels 731, 733, 735 by adjusting the LED 721 to a nominal value in the middle range of the broadband channel 737. Once the LED 721 is set to this value at the beginning of a treatment, the system monitors the red, blue, green channels 731, 733, 735 to watch for a rate change for the sensor 713 changing from yellow to blue as a function of ammonia gas detection within the dialysate, which is an indicator of ammonium leakage into the dialysate within the sorbent cartridge 303.

Figure 33:
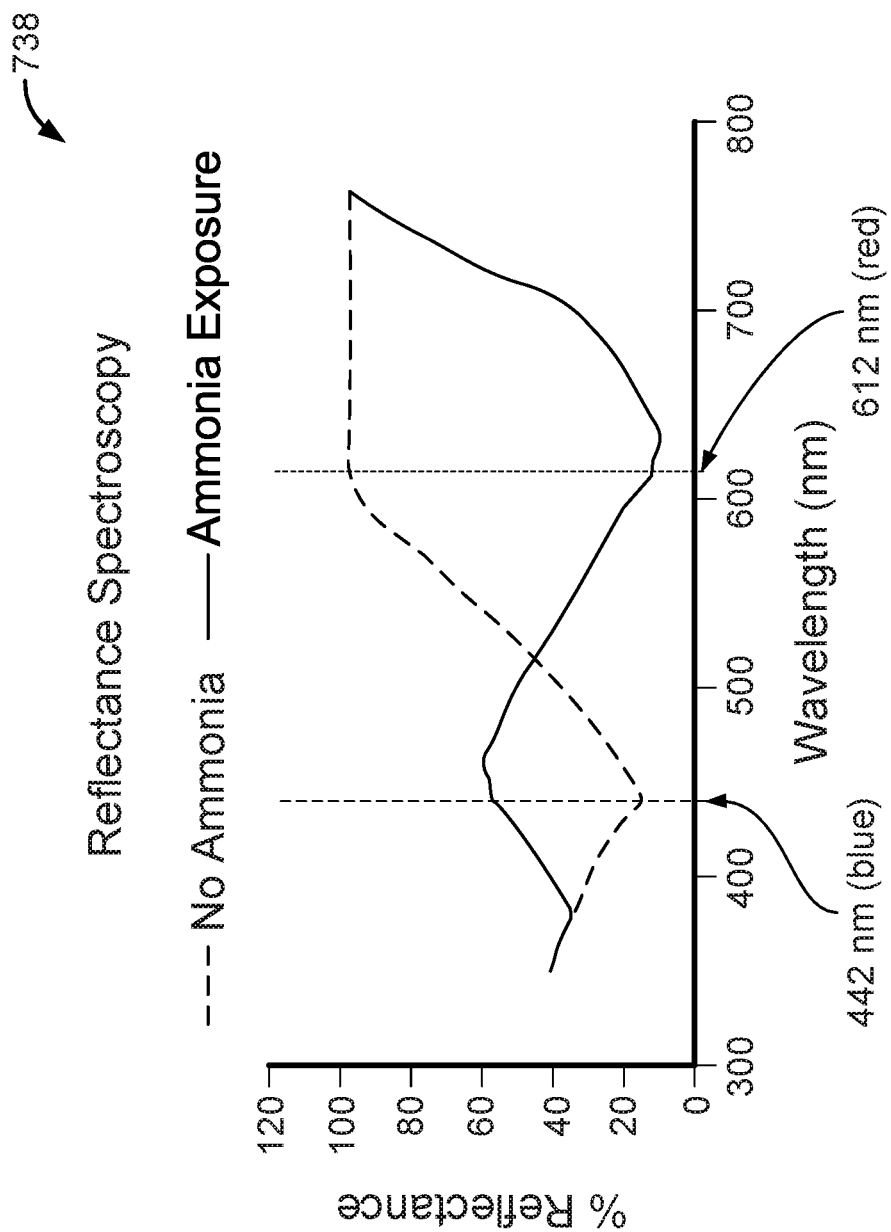
FIG. 33 is an example graph illustrating reflectance spectroscopy operational principles that apply to the ammonia detection system of FIG. 29.

Owing to light radiated by the LED 721 towards the ammonia sensor 165, the ammonia sensor 165 reflects light at certain wavelengths based on the color of the ammonia sensor 165. FIG. 33 illustrates the behavior of such reflected light according to reflectance spectroscopy principles in an example graph 738. Yellow light has wavelengths in a range of about 570 nm to about 640 nm, which is a mixture of visible red light and green light. Therefore, when the ammonia sensor 165 is yellow, the ammonia sensor 165 reflects light in both the red and green channels of the detector 728, with the highest color intensity corresponding to a visible red wavelength of about 612 nm. Blue color absorbs visible red light, while reflecting blue light. Therefore, when the ammonia sensor 165 changes from a yellow color to a blue color, there will be a reduction in an intensity of visible red light and an increase in an intensity of blue light reflected from the ammonia sensor 165, with the highest color intensity corresponding to a blue wavelength of about 442 nm.

A change in a ratio of the color intensity of blue light reflected from the sensor 713 to visible red light reflected from the sensor 713 (e.g., a ratiometric color intensity change) can be used to detect a certain increase in a concentration of ammonia within the dialysate, which corresponds to a certain degree of ammonium leakage into the dialysate as the dialysate circulates through the sorbent cartridge 303. As further shown in FIG. 33, the fraction of incident electromagnetic power incident at the sensor 713 (e.g., associated with the white light radiated from the LED 721) that is subsequently reflected by the sensor 713 is defined as reflectance (e.g., % reflectance), which can vary as a function of a wavelength of reflected light.

Figure 34:
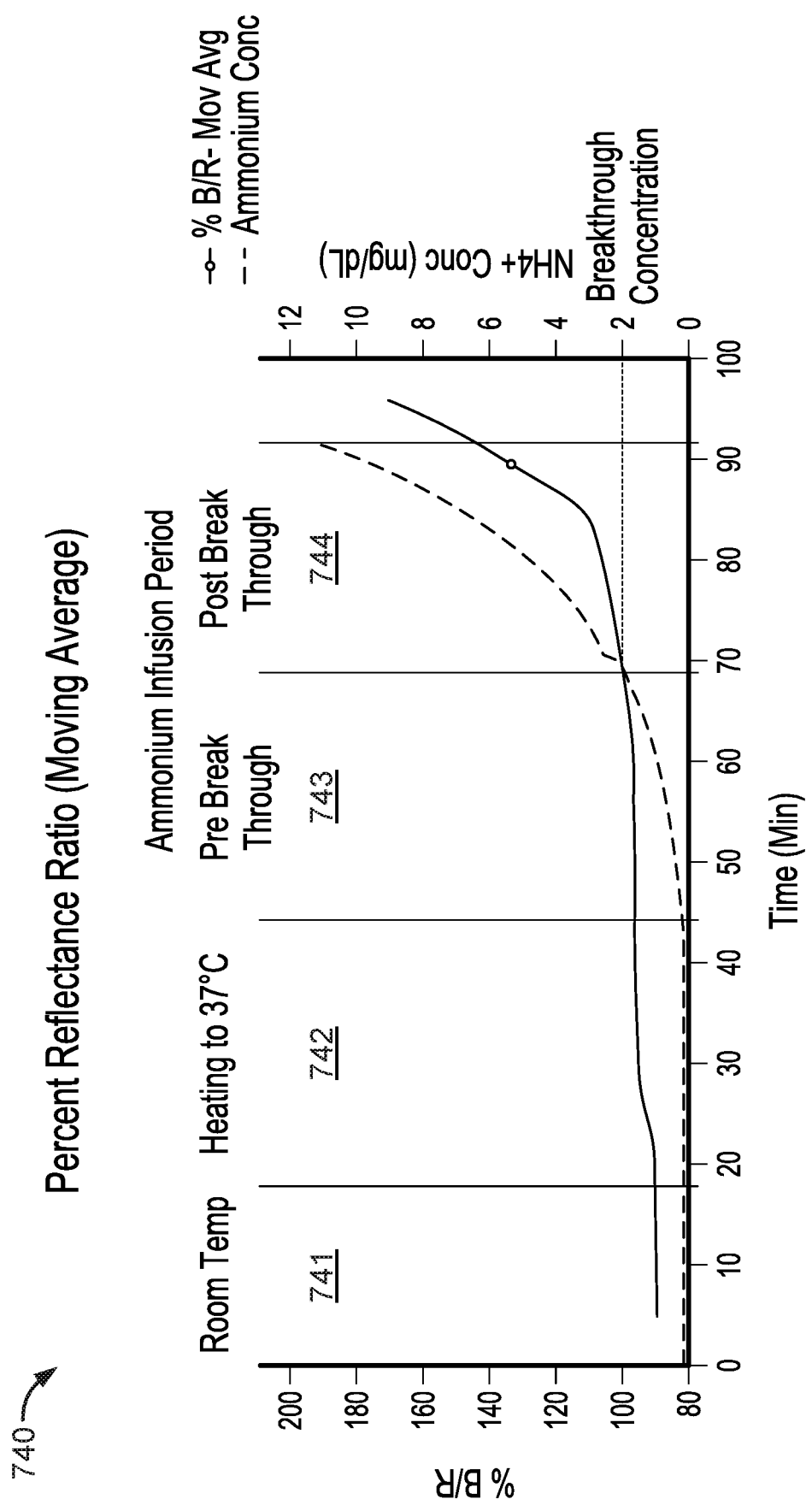
FIG. 34 is an example graph illustrating an analysis of percent reflectance ratio that can be generated according to the reflectance spectroscopy operational principles of the ammonia detection system of FIG. 29.

FIG. 34 provides an example graph 740 of a ratio of blue reflectance to red reflectance (e.g., a reflectance ratio) from the sensor 713 as a function of time during an ammonium infusion process carried out at a benchtop setup that includes the ammonia detection system 700 and the sorbent cartridge 303. Such analysis may be performed at one or both of the digital detector circuitry 720 of the ammonia detector 121 and circuitry that implements one or more processors of a control system, such as the processor 410 of the control system 161. The benchtop setup otherwise mimics the fluid flow parameters of the fluid conditioning system 100. The reflectance ratio is shown as a multiple of 100 (e.g., a percent reflectance ratio) and indicated as % B/R in the graph 740. Therefore, a percent reflectance ratio of less than 100 is measured when the intensity of blue light reflected from the sensor 713 is less than the intensity of red light reflected from the sensor 713, which corresponds to an ammonium concentration in the circulating dialysate that is below a certain breakthrough concentration (e.g., about 2 mg/dL) and to a yellow color of the sensor 713.

In contrast, a percent reflectance ratio of greater than 100 is measured when the intensity of blue light reflected from the sensor 713 is greater than the intensity of red light reflected from the sensor 713, which corresponds to an ammonium concentration in the circulating dialysate that is above the breakthrough concentration and to a blue color of the sensor 713. In some embodiments, the breakthrough concentration of about 2 mg/dL defines an exhaustion capacity point of the sorbent cartridge 303. In some embodiments, the breakthrough concentration is a multiple of a permissible ammonium concentration within the dialysate that may result from channeling or other mass transport inefficiencies. For example, the breakthrough concentration of about 2 mg/dL may be equal to about four times a permissible ammonium concentration of about 0.5 mg/dL within the circulating dialysate. In some examples, the ammonium concentration within the circulating dialysate may be four times or more greater than an ammonium concentration within the patient's blood since the total blood volume of the patient is typically at least four times as great as the volume of dialysate circulating within the fluid circuit 350. For example, a breakthrough ammonium concentration of about 2 mg/dL within the circulating dialysate may correspond to an ammonium concentration of about 0.5 mg/dL within the patient's blood. An ammonium concentration of about 0.5 mg/dL within the patient's blood which may correspond to an ammonia concentration about 7 µg/dL to about 10 µg/dL within the patient's blood (e.g., depending on a size of the patient), which is well below the toxic ammonia threshold concentration of about 100 µg/dL.

In the example graph 740, a moving average technique is applied to the reflectance ratio data (e.g., with a moving time window of 5 min and a sample collection rate of 0.42 s) to smoothen the curve of the percent reflectance ratio (e.g., to minimize effects due to noise factors). Therefore, a first data point on the curve of percent reflectance ratio does not appear until five minutes after the ammonium infusion process begins.

The ammonium infusion process includes first, second, third, and fourth phases 741, 742, 743, 744, respectively. In the first phase 741, circulating dialysate is maintained at a room temperature of about 15° C. to about 37° C. In some examples, the first phase 741 corresponds to the priming stage carried out by the fluid conditioning system 100 in which an initial volume of water is drawn into the fluid circuit 350 for subsequent creation of dialysate, as discussed above with respect to FIG. 20. In the second phase 742, the circulating dialysate is warmed to physiological temperature (e.g., about 37° C.). In some examples, the second phase 742 corresponds to the infusion stage carried out by the fluid conditioning system 100 in which bicarbonate, salt, and dextrose are added to the water in the fluid circuit 350 to produce dialysate, as discussed above with respect to FIG. 21.

In the third phase 743, ammonium is initially infused into the circulating dialysate and begins to accumulate exponentially in the dialysate up to the ammonium breakthrough concentration. In some examples, the third phase 743 may correspond to the first phase of the treatment stage carried out by the fluid conditioning system 100 in which bicarbonate solution is used to regulate a conductivity of the dialysate, as discussed above with respect to FIG. 22. In the fourth phase 744, ammonium continues to be infused into the circulating dialysate and to accumulate exponentially in the circulating dialysate beyond the breakthrough concentration. In some examples, the fourth phase 744 corresponds to the second phase of the treatment stage carried out by the fluid conditioning system 100 in which dilution water is used to regulate a conductivity of the dialysate, as discussed above with respect to FIG. 22.

Since the sensor 713 is initially yellow (e.g., unexposed to ammonia) at a start of the first phase 741, the percent reflectance ratio is initially less than 100, as the sensor 713 reflects visible light with more red intensity than blue intensity. The percent reflectance ratio climbs during the second phase 742 of the ammonium infusion process (e.g., despite continued limited exposure to ammonia) as a result of temperature-associated changes in reflectance spectroscopy. Following infusion of ammonium during the third phase 743, the percent reflectance ratio climbs to 100 (e.g., corresponding to the ammonium breakthrough concentration) as the sensor 713 is exposed to an increasing concentration of ammonia (e.g., generated from ammonium within the dialysate) and therefore reflects light with an increasingly blue intensity.

Analyzing reflectance at the sensor 713 as a ratio of blue and red color intensities magnifies the detection of ammonia within the circulating dialysate, as compared to analyzing reflectance at a sensor as absolute values of separate, individual blue and red color intensities according to conventional reflectance spectroscopy techniques for ammonia detection. For example, both the numerator and the denominator of the reflectance ratio can change (e.g., thereby causing a significant change in the value of reflectance ratio), whereas conventional techniques simply account for an absolute value of either a blue color intensity or an absolute value of a red color intensity of light reflected from an ammonia sensor. Examination of the reflectance as a ratio also avoids false alarm conditions that may otherwise be observed due to temperature-associated changes in reflectance spectroscopy using conventional techniques during a phase in which the dialysate is heated to physiological temperature, as will be discussed in more detail below with respect to FIG. 34.

In some embodiments, the sensor 713 may include natural variations caused by one or more of an assembly process, paper smoothness, and solution homogeneity (e.g., homogeneity in the coating of the bromocresol green and the malonic acid). For example, paper smoothness may change reflectance values of blue and red, which can lead to false alarms. In other cases, solution non-homogeneity on the sensor paper may result in a portion or all of the sensor 713 having a white color instead of a yellow color, which can result in different reflectance values and eventual false alarms. In some examples, undesired effects of such natural variations on the absolute value of the percent reflectance ratio may be addressed by alternatively examining a rate of change (e.g., a slope) of the percent reflectance ratio.

For example, FIG. 34 provides an example graph 750 of an instantaneous slope of the percent reflectance ratio of the graph 740. The graph 750 therefore reflects the moving average technique as applied to the percent reflectance ratio (e.g., with a moving time window of 5 min and a sample collection rate of 0.42 s). The slope is shown as a multiple of 1,000, and as shown in FIG. 34, the ammonium breakthrough concentration corresponds to a threshold slope (e.g., a slope of about 5 in this instance). As discussed above with respect to the graph 740, such analysis may be performed at the one or more processors 729 of the ammonia detector 121.

In some examples, the undesired effects of natural variations in the sensor 713 and various noise factors have a shorter duration in the slope analysis of the percent reflectance ratio (e.g., provided by the graph 750) as compared to the duration in the absolute value of the percent reflectance ratio (e.g., provided by the graph 740). For example, the temperature-related effects of heating the dialysate to physiological temperature persist from about 23 min to about 45 min in the graph 740, whereas in the graph 750, such effects begin at about 25 min, but begin to dampen shortly after this time. Events such as fogging of the either of the lenses 714, 722 may also persist for a shorter period of time in the curve of the slope as compared to the curve of the absolute value of the percent reflectance ratio.

Accordingly, in some embodiments, certain criteria may be imposed on the moving average analysis of the slope of the percent reflectance ratio in order to determine that the ammonia concentration in the dialysate has reached a certain threshold concentration. For example, such criteria may include that the slope be maintained at equal to or greater than the threshold slope for a minimum period of time (e.g., 1 min to about 15 min). Upon such criteria being met and associated data being sent from the one or more processors 729 to the control system 161, the control system 161 of the fluid conditioning system 100 may stop the treatment phase and trigger an alarm that is implemented via the one or more processors 410 of the control system 161. In some embodiments, the alarm provides an audible notification that alerts the patient or a nearby clinician that a problem has been identified with the treatment phase of the fluid conditioning cycle. In some embodiments, the alarm alternatively or additionally provides a visible notification, such as a message displayed on the display screen 148 (refer to FIG. 1), which may indicate that the sorbent cartridge 303 is exhausted or that the sorbent cartridge 303 should be replaced.

For the example analyses provided by the graph 750, a concentration of ammonia corresponding to an ammonium concentration that meets or exceeds the breakthrough ammonium concentration of about 2 mg/dL may be detected within about 20 minutes of starting ammonium infusion within the dialysate. In some examples, such behavior was observed with a sample size of three runs, an average ammonium leak detection time of about 12 min, a standard deviation of about 1.05 min, a dialysate flow rate of about 300 mL to about 400 mL, a dialysate temperature of about 36° C. to about 38° C., and a dialysate pH of about 6.5 to about 7.0. Following termination of the treatment phase due to ammonium leakage, the exhausted sorbent cartridge 303 can be removed and replaced with a fresh sorbent cartridge 303 in order to continue treatment.

Various modifications may be made to any of the above-discussed embodiments without departing from the spirit and scope of the above disclosures. For example, while the moving average techniques applied to the percent reflectance ratio and the slope of percent reflectance ratio have been described as including a moving time window of about 5 min, in other embodiments, analyses that are otherwise similar to the analyses described above may utilize a moving time window of a different period, such as about 0.1 min or about 50 min.

While the sensor 713 has been described as being coated with bromocresol green and malonic acid, in some embodiments, an ammonia sensor that is otherwise substantially similar in construction and function to the ammonia sensor 165 may include a sensor that is coated with one or both of a different acid base indicator and a different acid.

Figure 35:
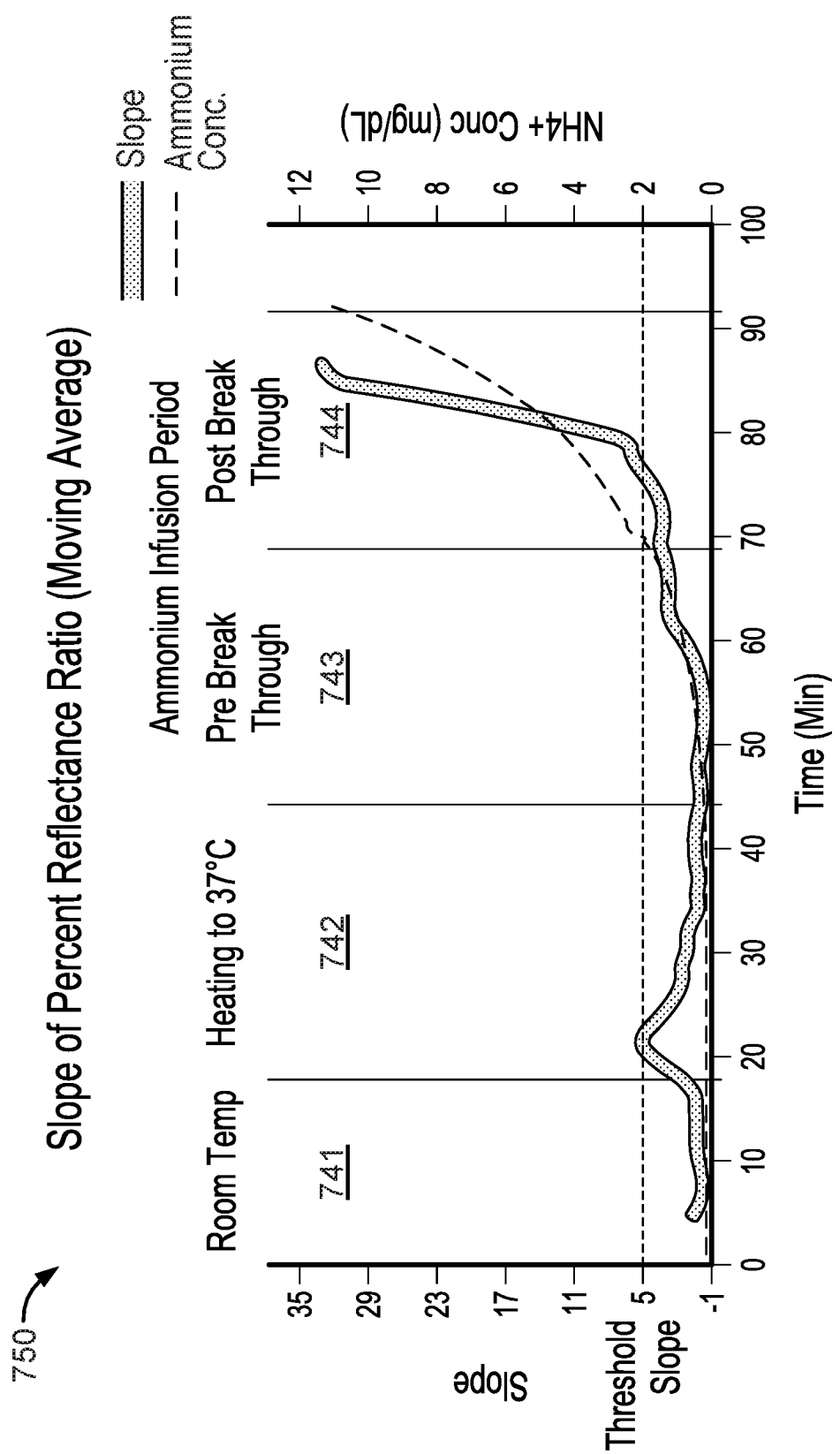
FIG. 35 is an example graph illustrating an analysis of a moving average slope of the percent reflectance ratio of FIG. 34.
Figure 37:
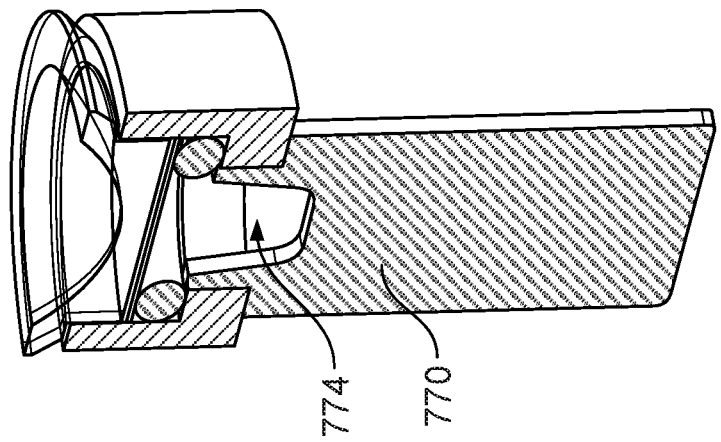
FIG. 37 is a cross-sectional perspective view of a baffle of an ammonia sensor.
Figure 36:
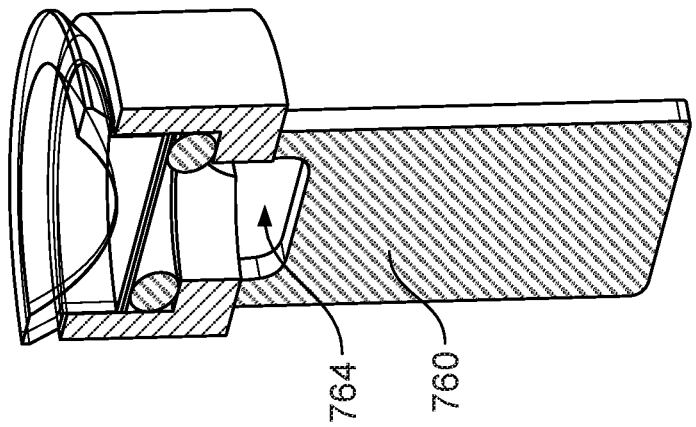
FIG. 36 is a cross-sectional perspective view of a baffle of an ammonia sensor.

While the baffle 715 has been described and illustrated as including the base 730 and the protrusion 732, in some embodiments, an ammonia sensor that is otherwise substantially similar in construction and function to the ammonia sensor 165 may include a baffle that has different profile. For example, FIGS. 35-37 respectively illustrate baffles 760, 770, 780 that define cross-sectional flow areas 764, 774, 784 with a different shape or size than the annular cross-sectional flow area 734 and that accordingly generate different turbulence behavior within a dialysate fluid flow.

Figure 38:
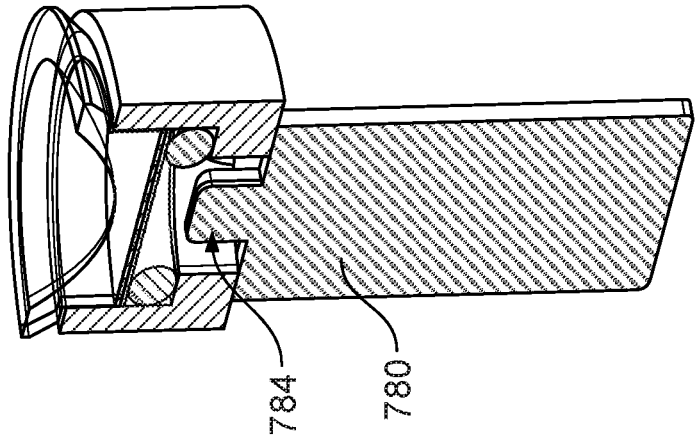
FIG. 38 is a cross-sectional perspective view of a baffle of an ammonia sensor.

In some embodiments, an ammonia sensor that is otherwise similar in construction and function to the ammonia sensor 165 may include a connector body with a form that is different from that of the connector body 707. For example, FIG. 38 illustrates an ammonia sensor 790 with such a connector body 797. The connector body 797 includes inlet and outlet flow channels 791, 792 that are oriented at an angle of about 20 degrees to about 90 degrees from a central axis 791 of the ammonia sensor 790. Such configuration of the flow channels 791, 792 is designed to generate turbulence within the dialysate fluid flow such that the ammonia sensor 790 does not include a baffle. The ammonia sensor 790 otherwise includes the membrane 711, the snap ring 712, the sensor 713, and the lens 714 of the ammonia sensor 165.

While the ammonia detection system 100 has been described and illustrated as utilized in dialysate systems, in some embodiments, an ammonia detection system that is similar in construction and function to the ammonia detection system 100 may be utilized in any type of system where ammonium or ammonia release presents a problem and that therefore requires ammonia detection within a circulating fluid, such as other types of systems that are unrelated to dialysis or other types of dialysis systems that do not include a sorbent cartridge.

While the ammonia detection system 700 and the sorbent cartridge 303 have been described and illustrated as separate devices in the fluid conditioning system 100, in some embodiments, a sorbent cartridge that is otherwise similar in construction and function to the sorbent cartridge 303 may include either or both of a built-in (e.g., integral) ammonia sensor and ammonia detector that are similar in function and similar in construction in many aspects to the ammonia sensor 165 and the ammonia detector 121 of the ammonium detection system 700.

While the fluid conditioning system 100 has been described and illustrated as including the pressure transducers 119 (PT1, PT2, PT3, PT4) for regulating pump flow rates, in some embodiments, a fluid conditioning system that is otherwise similar in construction and function to the fluid conditioning system 100 may alternatively include flow meters instead of pressure transducers for regulating pump flow rates. In some embodiments, a fluid conditioning system that is otherwise similar in construction and function to the fluid conditioning system 100 may not include pressure transducers or flow meters and may instead be RPM-controlled based on a detailed knowledge of the system operation to regulate pump flow rates.

While the fluid conditioning system 100 has been described and illustrated as including peristaltic pumps 103, 104 (P1, P2, P3, P4), in some embodiments, a fluid conditioning system that is otherwise similar in construction and function to the fluid conditioning system 100 may alternatively include a different type of pump, such as an impeller pump, a linear displacement pump, positive displacement pump, or a centrifugal pump.

While the fluid conditioning system 100 has been described and illustrated as including one overflow reservoir (e.g., the secondary reservoir 305), in some embodiments, a fluid conditioning system that is otherwise similar in construction and function to the fluid conditioning system 100 may include one or more additional overflow reservoirs. For example, in some embodiments, an additional reservoir may be connected to the fluid circuit 350 upstream of pump P1 or downstream of pump P2. In some embodiments, an additional reservoir may have a capacity different than that of either reservoir 304 or reservoir 305 or may have a zero volume capacity. In some embodiments, a reservoir may be permanently connected to a drain.

While the heater bag 153 has been described and illustrated as being arranged downstream of pump P2 of the fluid conditioning system 100, in some embodiments, a fluid conditioning system that is otherwise similar in construction and function to the fluid conditioning system 100 may include a heater bag or other heating element that is arranged at a different location along the fluid circuit 350 in order to achieve optimal temperature control of fluid flowing through the fluid circuit 350. For example, in some embodiments, a heater bag may be positioned immediately downstream of the sorbent cartridge 303 and may be powered based on signals from temperature sensor T1 to ensure that the temperature of the dialysis fluid is not high enough to damage internal components of the sorbent cartridge 303. In some embodiments, a heater bag may be located along the fluid circuit 350 anywhere between valve V1 and valve V2, as advantageous (e.g., to promote dissolution of the dry chemicals in the supply bags 306, 307, 309).

While the fluid conditioning system 100 has been described as including three-way valves V1-V7, in some embodiments, a fluid conditioning system that is otherwise similar in construction and function to the fluid conditioning system 100 may alternatively include one or more two-way valves to achieve the fluid flow path scenarios discussed above.

While an operation of the fluid conditioning system 100 has been described and illustrated with respect to certain flow rates, fluid volumes, temperatures, pressures, and time periods, in some embodiments, the fluid conditioning system 100 may be operated to carry out a fluid conditioning cycle with one or more different flow rates, fluid volumes, temperatures, pressures, and time periods, while still functioning to adequately condition dialysate for use in a cooperating dialysis system.

Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them. A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

Other embodiments are within the scope of the following claims.

What is claimed is:

1. A spectroscopic detection system, comprising:
a sensor configured to reflect light of a first wavelength associated with a presence of a first substance on the sensor and configured to reflect light of a second wavelength associated with a presence of a second substance on the sensor, the second substance delivered to the sensor from a flowing fluid;
a detector configured to receive the light of the first and second wavelengths reflected from the sensor; and
one or more processors in electrical communication with the detector and configured to identify an excess condition of the second substance with respect to the flowing fluid based on a second amount of the light of the second wavelength received at the detector and a first amount of the light of the first wavelength received at the detector.

2. The spectroscopic detection system of claim 1, wherein the sensor comprises an acid base indicator that is sensitive to a pH of the second substance.

3. The spectroscopic detection system of claim 2, wherein the first substance is an acidic substance, wherein the sensor is of a first color in an initial state in which the first substance is present on the sensor and in which the second substance is not present on the sensor, and wherein the sensor is of a second color in a subsequent state in which both the first and second substances are present on the sensor.

4. The spectroscopic detection system of claim 1, further comprising one or more lenses arranged to focus the light of the first and second wavelengths reflected from the sensor onto the detector.

5. The spectroscopic detection system of claim 1, further comprising an LED that is configured to radiate broadband light onto the sensor, wherein the sensor is configured to reflect a first portion of the broadband light as the light of the first wavelength and a second portion of the broadband light as the light of the second wavelength.

6. The spectroscopic detection system of claim 1, further comprising a membrane that is permeable to the second substance and positioned upstream of the sensor.

7. The spectroscopic detection system of claim 1, further comprising a housing that supports the sensor and that is configured to absorb ambient light.

8. The spectroscopic detection system of claim 1, wherein the sensor is oriented parallel to a bulk flow direction of the flowing fluid and orientated perpendicular to a flow of the second substance towards the sensor.

9. The spectroscopic detection system of claim 8, further comprising a flow obstruction that is oriented perpendicular to the bulk flow direction of the flowing fluid and that generates turbulence in a bulk flow of the flowing fluid.

10. The spectroscopic detection system of claim 9, wherein the flow obstruction is configured to increase a velocity of the bulk flow of the flowing fluid.

11. The spectroscopic detection system of claim 1, wherein the sensor comprises a paper material.

12. The spectroscopic detection system of claim 1, further comprising a connector body that houses the sensor and that is configured to be assembled with a fluid line of a fluid cassette, wherein the connector body is arranged to receive a bulk flow of the flowing fluid from a device configured to remove a precursor chemical of the second substance from the flowing fluid.

13. The spectroscopic detection system of claim 1, wherein the first amount of the light of the first wavelength comprises a first percent reflectance of a first color associated with the light of the first wavelength, and wherein the second amount of the light of the second wavelength comprises a second percent reflectance of a second color associated with the light of the second wavelength.

14. The spectroscopic detection system of claim 1, wherein the excess condition comprises an increase in a concentration of the second substance within the flowing fluid, and wherein the increase in the concentration of the second substance corresponds to an increase in a concentration of a precursor chemical of the second substance to a value that is about equal to or greater than a threshold concentration of the precursor chemical.

15. The spectroscopic detection system of claim 1, wherein the one or more processors are configured to identify the excess condition by determining a moving average of a ratio of the second amount of the light of the second wavelength received at the detector to the first amount of the light of the first wavelength received at the detector.

16. The spectroscopic detection system of claim 15, wherein the one or more processors are configured to identify the excess condition by determining a rate of change of the ratio.

17. The spectroscopic detection system of claim 16, wherein the one or more processors are configured to identify the excess condition by comparing the moving average of the ratio to one or more criteria.

18. The spectroscopic detection system of claim 1, wherein the one or more processors are configured to transmit data associated with triggering of an alarm notification upon identification of the excess condition.

19. The spectroscopic detection system of claim 1, wherein the sensor is disposable and the detector is reusable.

20. The spectroscopic detection system of claim 1, wherein the flowing fluid comprises circulating dialysate and the monitored substance comprises ammonia.

21. A dialysis system, comprising:
a sorbent cartridge configured to remove a precursor substance from dialysate flowing within the dialysis system, the precursor substance being a precursor to a first substance that reflects light of a first wavelength; and
a spectroscopic detection system for identifying an excess condition of the first substance with respect to the dialysate, the spectroscopic detection system comprising:
a sensor configured to reflect light of a second wavelength associated with a presence of a second substance on the sensor and configured to reflect light of the first wavelength associated with a presence of the first substance on the sensor, the first substance flowing to the sensor from the dialysate,
a detector configured to receive the light of the first and second wavelengths reflected from the sensor, and
one or more processors in electrical communication with the detector and configured to identify the excess condition of the first substance with respect to the dialysate based on a first amount of the light of the first wavelength received at the detector to a second amount of the light of the second wavelength received at the detector.

22. A method of detecting a substance within a flowing fluid, the method comprising:
delivering a first substance to a sensor with the flowing fluid, the first substance being capable of reflecting light of a first wavelength;
reflecting light of a second wavelength from the sensor based on a presence of a second substance on the sensor and reflecting light of the first wavelength from the sensor based on a presence of the first substance on the sensor;
receiving the light of the first and second wavelengths reflected from the sensor at a detector; and
identifying, at one or more processors in electrical communication with the detector, an excess condition of the first substance with respect to the flowing fluid based on a first amount of the light of the first wavelength received at the detector and a second amount of the light of the second wavelength received at the detector.

* * * * *